United States Patent [19]
Sternberg et al.

[11] 3,979,589
[45] Sept. 7, 1976

[54] METHOD AND SYSTEM FOR THE INFRARED ANALYSIS OF GASES

[75] Inventors: Stanley R. Sternberg, Ypsilanti; James E. Young, Detroit; John W. Lennington, Ypsilanti, all of Mich.

[73] Assignees: Finn Bergishagen; John S. Abbott; Kenneth A. Hutchinson; James E. Young; John W. Lennington; Stanley R. Sternberg, all of Union Lake, Mich.

[22] Filed: Mar. 31, 1975

[21] Appl. No.: 563,709

Related U.S. Application Data

[60] Division of Ser. No. 420,305, Nov. 29, 1973, Pat. No. 3,887,473, which is a division of Ser. No. 281,958, Aug. 18, 1972, Pat. No. 3,790,798, which is a continuation-in-part of Ser. No. 178,260, Sept. 7, 1971, Pat. No. 3,790,797, which is a continuation-in-part of Ser. No. 809,752, March 24, 1969, abandoned.

[52] U.S. Cl. .............................. 250/252; 250/345; 250/565
[51] Int. Cl.² ........................................ G01D 18/00
[58] Field of Search .......... 250/252, 345, 564, 565, 250/343, 344; 356/81, 82, 97, 204, 205

[56] References Cited
UNITED STATES PATENTS

| | | | |
|---|---|---|---|
| 3,562,522 | 2/1971 | Cederstrand et al. | 250/252 |
| 3,734,631 | 5/1973 | Justice et al. | 250/345 |
| 3,787,124 | 1/1974 | Lowy et al. | 250/565 |

*Primary Examiner*—Alfred E. Smith
*Assistant Examiner*—D. C. Nelms
*Attorney, Agent, or Firm*—Harness, Dickey & Pierce

[57] ABSTRACT

A dual path analyzer and a single path analyzer are disclosed, each for determining the concentration of one or more gaseous components in a mixture of gases. The preferred analyzer is a single path instrument which includes a source of infrared energy, a detector for the energy, a sample cell for the gas mixture positioned between the source and detector, and a filter wheel having a plurality of filters and a source blocking device positioned between the sample cell and detector for sequentially interposing the filters and the source blocking device between the source and the detector. Means are provided for amplifying the output signal of the detector and for processing the signal to provide a direct readout display which indicates the concentration of the gaseous components being analyzed. The processing electronics preferably include provision for calibrating the analyzer with clean ambient air, for compensating for background levels of radiation, and for correcting the displayed output signal for the effects of absorption band interferences between two or more gases in the gas mixture. The structure of the dual path analyzer includes a source of infrared energy, a detector for the energy, a sample cell for the gas mixture, a cell for a reference gas, and optical path means between the source and detector for sequentially directing the source energy through the sample cell, the reference cell, and through neither cell. Processing electronics similar to the single path instrument can be incorporated to compensate for background radiation and absorption band interferences.

28 Claims, 23 Drawing Figures

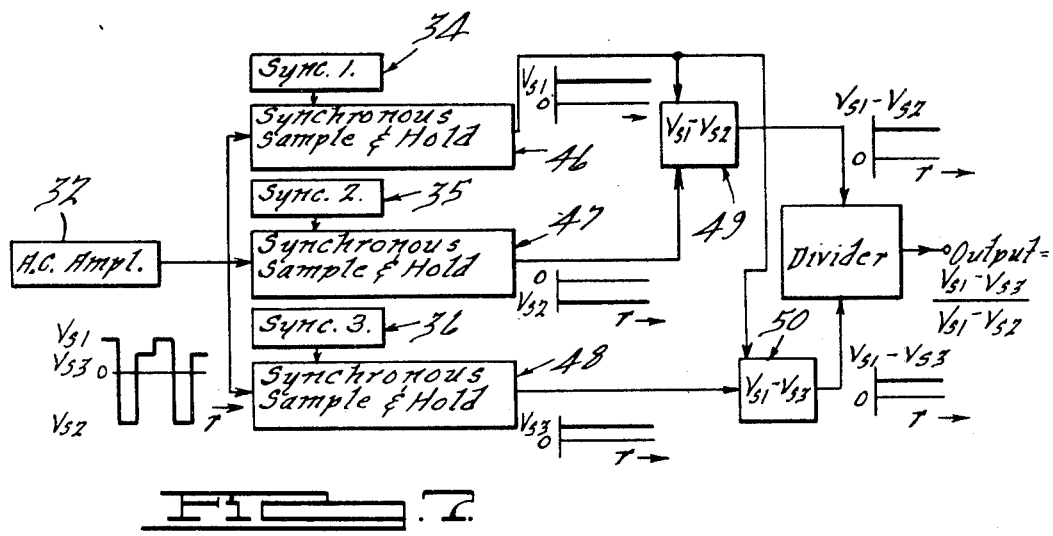
FIG. 7.
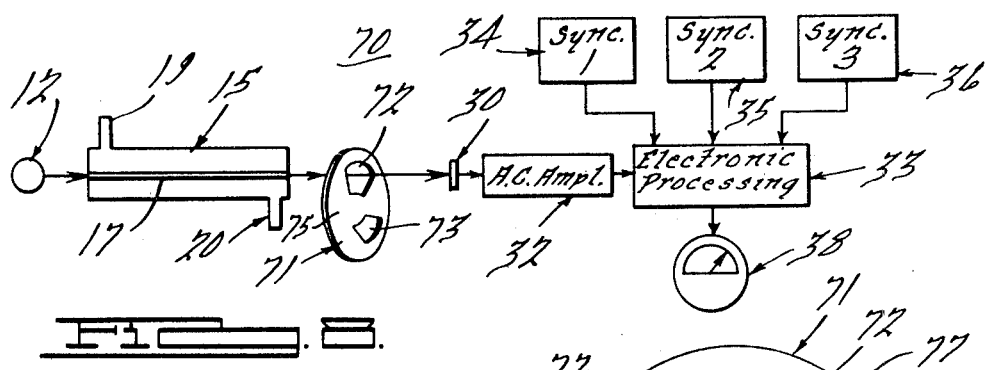
FIG. 8.
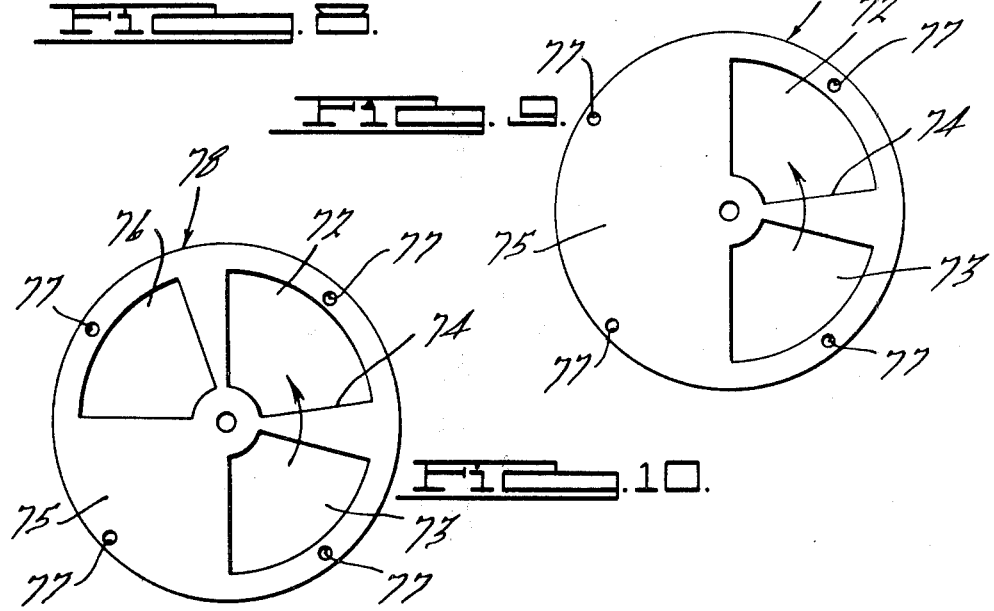
FIG. 9.
FIG. 10.

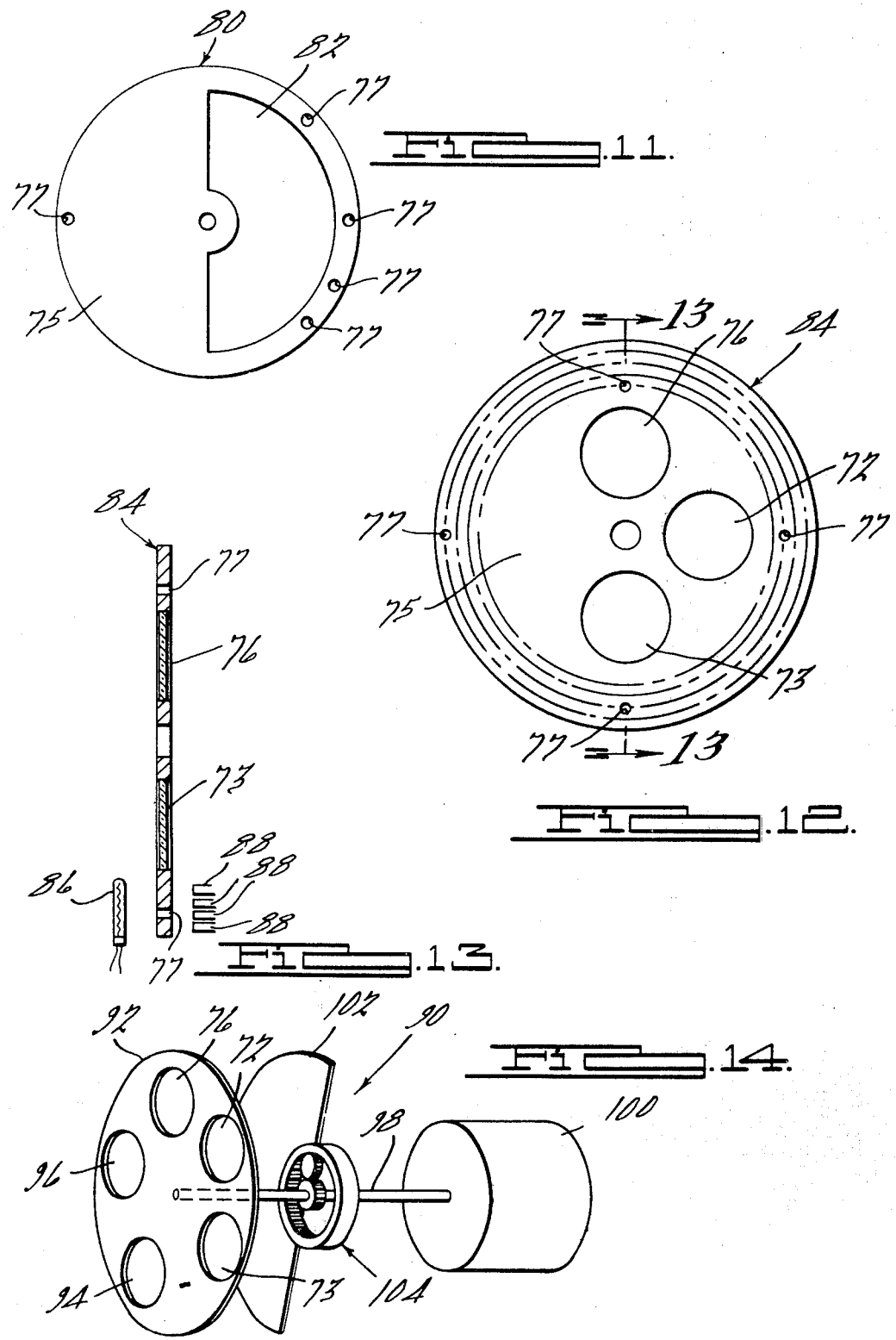

METHOD AND SYSTEM FOR THE INFRARED ANALYSIS OF GASES

CROSS REFERENCE TO RELATED APPLICATIONS

This is a division of application Ser. No. 420,305, filed Nov. 29, 1973 now U.S. Pat. No. 3,887,473 which is a division of application Ser. No. 281,958 filed Aug. 18, 1972, now U.S. Pat. No. 3,790,798, which is a continuation-in-part of application Ser. No. 178,260 filed Sept. 7, 1971, now U.S. Pat. No. 3,790,797 which in turn is a continuation-in-part of application Ser. No. 809,752 filed Mar. 24, 1969, now abandoned.

BACKGROUND AND SUMMARY OF THE INVENTION

This invention relates to the analysis of gas mixtures and refers more specifically to gas analyzers for determining the concentration of a constituent in a mixture of gases, e.g. automobile exhaust gases or the like. The enactment of federal and state legislation to control automobile emissions has resulted in a requirement to measure automobile emissions outside of the laboratory. Several portable automobile emissions analyzers have appeared in the last few years, all claiming to fill the need for quick, easy accurate measurement of exhaust gaseous concentrations. Almost without exception, the measurement techniques employed in these portable analyzers are identical with those used in their more costly and more complex laboratory counterparts. However, the compromises required to employ these techniques in low cost, portable packages combined with the lack of skill of their intended operators and the hostility of their intended environment has resulted in a generation of instruments which are far from ideal.

The present invention provides a portable gas analyzer which quickly, easily and accurately determines the concentration of one or more gaseous components of a mixture of gases. A gas analyzer of the present invention requires no span gases for calibration; the instrument is calibrated by a zeroing procedure which utilizes ordinary air. The background level of radiation is determined and is used to appropriately compensate the output signals of the analyzer so that true indications of the concentration of gaseous components under investigation are obtained.

In a preferred single path embodiment, the analyzer includes a source of radiant energy, preferably infrared energy; a detector for the radiant energy; means for interposing the gas mixture between the source and the detector, for example, a sample cell; means for sequentially interposing a reference filter, a filter for each gaseous component under investigation, and a source blocking device between the source and the detector; means for compensating the output signal of the detector in accordance with the background level of radiation as determined when the source blocking device is interposed between the source and the detector; and means for compensating the gaseous components under investigation for absorption band interferences. With the above signal processing system, an output signal may be provided which may be displayed substantially in real time.

By way of example, the source blocking means, the filter for each gaseous component under investigation, and the reference filter may be mounted on a wheel which is positioned between the sample cell and the detector, preferably in close proximity to the detector so that the filter wheel and components constitute substantially the only source of background radiation whereby the background contribution to the signals is closely controlled and accurately determined. However, each of the above may be positioned in any suitable location intermediate the source and the detector. Also, by way of example, the background signal obtained when the source blocking means is interposed between the source and the detector may be stored for sequential subtraction from each output signal corresponding to the respective gaseous components under investigation as well as from a reference signal. By measuring each of the component, reference, and background signals independently of all previous measurements of the component, reference, and background signals on each cycle and subtracting the background signal from at least one of the signals on each cycle, the DC component of noise and a substantial portion of the low frequency component of noise is removed on each cycle. Consequently, there are no systematic errors since the means noise level is zero. That is to say, if the output signal is time averaged over a sufficiently long time, an error free signal can be obtained.

Compensation for absorption band interferences may be accomplished in a similar manner by storing and sequentially utilizing a signal representative of each interfering gaseous component. In the preferred form, each of the signals corresponding to the gaseous components under investigation are normalized by providing a ratio of the gaseous component signals and the reference signal, the reference signal having been obtained when a filter having a spectral bandpass at which the gaseous components under investigation have negligable absorption is interposed between the source and the detector. This is advantageously accomplished using an analog divider incorporating a photocell and an associated radiant source. More particularly, the photocell is disposed in a feedback circuit of an operational amplifier to adjust the circuit gain in accordance with the resistance of the photocell. A light source is used in association with the photocell which is intensity-controlled by the reference signal level appearing at the output of the operational amplifier to correspondingly affect the gain of the operational amplifier by changing the resistance of the photocell. In effect, a highly effective, yet simple, analog divider is provided.

The above described processing circuitry for the single path analyzer may be also used with a dual path design with slight modification to accommodate the derivation of a reference signal through the use of a separate cell containing a reference gas rather than the aforementioned reference filter.

BRIEF DESCRIPTION OF THE DRAWINGS

FIG. 7 is a block and line diagram illustrating an electronic procedure and processing network or system for obtaining the subtractive output signal values just mentioned, whether in the case of a single or multiple filter arrangement, appropriate output-time graphed comparisons being appended;

FIG. 8 is a schematic lay-out of an alternative, single path, multiple filter type analytic system embodying special spectral filters and chopper device in combination with a sample cell;

FIGS. 9–12 are face views of alternative embodiments of the rotary chopper filter device employed with the embodiment of FIG. 8;

FIG. 13 is a cross-sectional view of the rotary chopper and filter device of FIG. 12 further illustrating an elongated light source and a plurality of photocells associated with the rotary chopper and filter device of FIG. 12;

FIG. 14 is a perspective illustration of an alternative embodiment of a rotary chopper and filter device which may be employed with the embodiment of FIG. 8;

DESCRIPTION OF THE PREFERRED EMBODIMENTS

Figure 1:
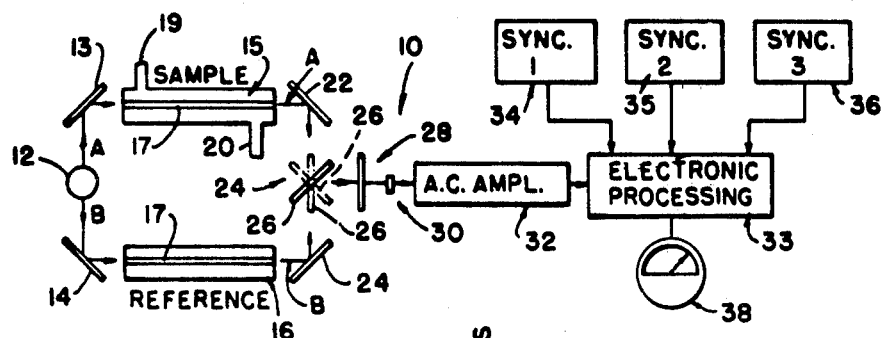
FIG. 1 is a schematic layout of a basic system of a single filter two-path type constituting one embodiment of the invention, however, this layout will also serve as a basis on which to describe various optical and electrical effects and calculations that also underlie other embodiments, whether of a multiple path or one-path type.

FIG. 1 very schematically illustrates one embodiment or system according to the invention, generally designated by the reference numeral 10, which is not necessarily the preferred one of the several forms herein shown and described, but which will nevertheless serve as a basis for a description of various spectral analysis effects and mathematical descriptions which will follow. Such descriptions, and electrical circuitry which carry them into practice, involve a subtractive comparison of proportionate output signals from a detector which (a) pertain to a sample cell-transmitted. cell-transmitted, attenuated beam and (b) to a comparison or reference beam. One of these comparative determinations invokes subtraction of a signal reflecting a zero or minimal impingement radiant energy, i.e. a background signal, from the reference derived signal on the detector; the other determination involves the subtraction of the sample signal from the reference signal. The result of the second or other subtractive comparison is then divided by the result of the first to obtain the desired fractional reading. If the concentrations of more than one gaseous component of the mixture of gases are to be determined, it is preferred to subtract the background level from each component signal in sequential, discrete steps. It will be appreciated that, in the previously described method, the background signal is directly subtracted from the reference signal in the first comparative determination while the second comparative determination, the sample signal which includes the background signal as a component thereof, is subtracted from the reference signal. Accordingly, the background signal is subtracted in each of the comparative determinations. In other words, it can be readily seen that the determinations made in each of the above described processes are mathematically equivalent.

As indicated, these effects, as herein specifically described, deal with the infrared portion of the spectrum; and the evaluations apply equally to each illustrated embodiment. Indeed, while the disclosure herein relates in the main to the special spectral absorption analysis of carbon monoxide, a field presently having great public interest, the principle and circuitry shown are equally well adapted for the infrared, visible or ultraviolet spectral analysis of various other media, as will be appreciated by those skilled in the art.

As illustrated in FIG. 1, the reference numeral 12 designates an appropriate source or emitter of infrared energy, of one of a number of known types. Attendant to its emission of infrared in the surrounding space, the emitter 12 directs 180° opposed beams A and B onto 45° angled fixed mirrors 13, 14, respectively, which fold the respective radiations through sample and reference cells 15, 16, respectively, an average beam path being indicated at 17 in each instance. The sample cell 15, as utilized in checking percent CO content of an automobile exhaust, will be equipped with appropriate inlet and outlet passages 19, 20, respectively, the former being appropriately connected perhaps via a pump to the exhaust manifold or muffler of the automobile. If desired, appropriate similar means may be provided for circulating the reference gas in cell 16.

An appropriate sampling line or system (not shown) is used to deliver a representative sample of engine exhaust gas to the intake 19 of cell 15 in a suitable form for analysis. Since carbon monoxide measurement is considered very important as an accurate indicator of engine efficiency, the sampling line must therefore deliver the exhaust sample without disturbing the relative concentration of carbon monoxide, i.e., it should be inert to carbon monoxide at elevated temperature. To this end stainless steel or plastics such as polytetrafluoroethylene, polyethylene, etc. can be used. The important criteria are that the sampling line be flexible and be resistant to elevated temperatures. For this reason, stainless steel tubing, either rigid or flexible, should be used in the front part of the sampling line, immediately in contact with the exhaust gas exiting for analysis.

The exhaust gas then passes to a water trap which serves to collect coalesced water in the exhaust gas. An automatic drain trap such as Arrow Model 5100 can be used for this purpose. Next, the sample passes into a pump, which forwards it to the infrared cell 15 for measurement.

Resuming, in reference to FIG. 1, the infrared beam component A, as reflected by mirror 13, traverses the path 17 and impinges a fixed 45° mirror 22 at the opposite end of sample cell 15, by which it is reflected onto a double sided movable mirror device, generally designated 24, three discrete positions of which are indicated in solid, dotted and dot-dash line in FIG. 1.

On the other hand, the infrared beam or ray component B emanating from source 12, deflecting from the fixed 45° mirror 14, traverses the reference cell 16, in which a gas other than the sample in cell 15 is contained or circulated. Exiting the reference cell 16, the beam B is reflected from a fixed mirror 24 positioned at 90° to the fixed mirror 22 and, which, like the latter, reflects the beam onto the side of the movable mirror device 24 opposite that impinged by the sample cell beam A.

Figure 2:
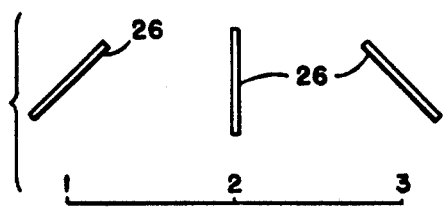
FIG. 2 is a schematic view showing three positions occupied by a movable mirror involved in the operation of the system of FIG. 1.

The device 24 comprises, as very schematically shown in FIG. 2, a mirror 26 which is reflective on both of its sides, so that in the position designated "1" in that figure (solid line in FIG. 1) the mirror 26 will receive and reflect the infrared reference beam portion B from source 12, as it has traversed the reference cell 16, through a spectral filter 28 and onto a radiant energy sensitive detector 30.

On the other hand, as the infrared beam portion A reflects from mirror 13 and traverses sample cell 15, it is folded back by mirror 22 onto the other side of mirror 26, as in its right hand position "3" of FIG. 2, (dotted line position in FIG. 1) to impinge filter 28. In the intermediate position "2" (dot-dash line in FIG. 1) the mirror 26 of course reflects no radiant energy, or a very minimal value.

It is assumed for present purposes that the mirror 26 shall move instantaneously between positions "1", "2", and "3" and return, but the speed of the transitions has no real bearing upon the operation of the system 10.

Thus, as the moving optical device 24 cycles through the positions "1", "2" and "3" of FIG. 2, the radiation B in position "1" which has passed through the reference cell 16 containing the reference gas will be passed through the filter device 28 and onto the detector 30. While the mirror is in position "2", no radiation emitted by the source 12 will be directed towards the detector. While it is in position "3" it is the radiation A passing through the sample cell 15 which will be directed through the spectral filter 28 and onto the detector 30.

It is contemplated that photoelectric or like pickups will be associated with the drive for movable mirror 26 to sense the position, "1", "2" or "3" of the movable mirror 26, and back to position "3", and to in turn trigger the sync means later referred to.

Traversing the filter device 28, the beam impinges the detector 30, the output signal of the detector influencing an alternating current amplifier system 32, to be described, the output of which passes to an electronic processing system 33 (also to be described). This system is triggered by synchronous pulse-generating units, such as are designated "sync-1", "sync-2", and "sync-3" in FIG. 1. The output of electronic processing network 33 goes to an appropriate meter or equivalent indicator 38 calibrated for a reading out of the percentage sample gaseous content which it is desired to ascertain.

Figure 3:
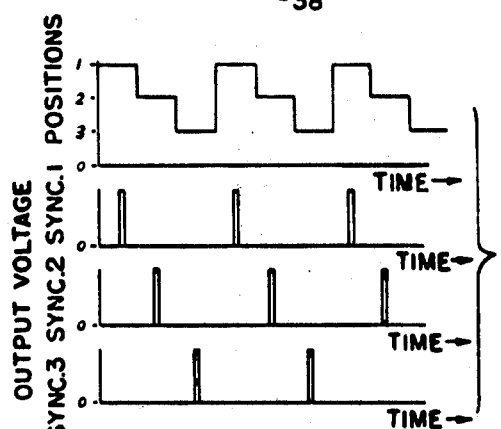
FIG. 3 graphically depicts the relationship in point of time between the three mirror positions typified in FIG. 2, and the three channels of synchronization pulses.
Figure 4:
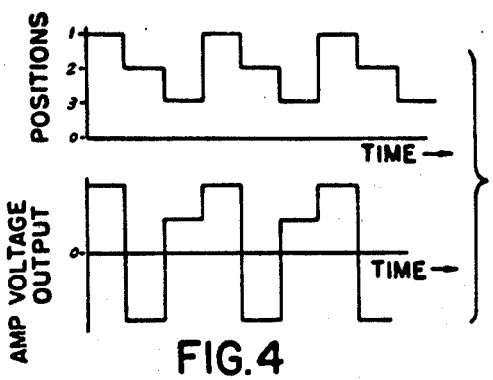
FIG. 4 similarly graphs the time relationship between mirror position and signal output following A.C. amplification.
Figure 5:
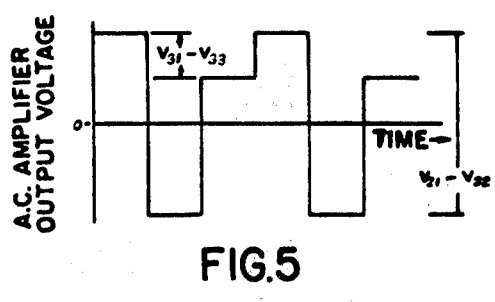
FIG. 5 is a time-plot of measurable quantities of A.C. amplifier output signals $V_{s1}V_{s2}$ and $V_{s3}$ which are ultimately used to obtain the values $V_{s1}-V_{s2}$ and $V_{s1}-V_{s3}$.
Figure 6:
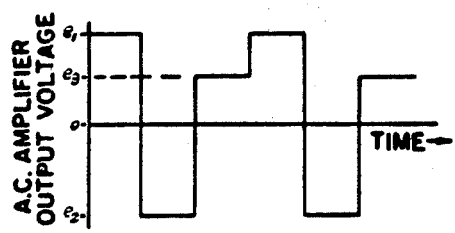
FIG. 6 is a graph plotting the several A.C. amplified output signals $V_{s1}-V_{s2}$ and $V_{s1}-V_{s3}$ dealt with herein, in relation to one another and time.

The sync devices 34, 35 and 36 generate narrow trigger impulses while the movable mirror is in positions 1, 2 and 3, respectively. FIG. 3 graphically shows the time relation between the mirror position and the occurrence of the pulses in each of the three sync channels, as descriptively designated. FIGS. 4–6 graph various time and signal relationships of a related nature.

For the detector of FIG. 1 a detector such as a lead selenide-type or indium antimonide photoconductive cell operating at ambient temperature is proposed. Many other detectors could be used, with slight modification in the following analysis. For these detectors, as for most quantum detectors, one can describe the detector's short-circuit current $I_s$ in amperes as follows (assuming unity bias voltage):

$I_s = qA_d \int n(\lambda) \; N(\lambda) \; d\lambda$, where $q$ = electronic charge (coulombs)

$A_d$ = detector area (cm$^2$)

$n(\lambda)$ = spectral quantum efficiency (dimensionless); and $N(\lambda)$ = spectral photon flux (cm$^{-2}$sec$^{-1}\mu^{-1}$)

Using this relation, we obtain the detector short-circuit current when the movable mirror 26 is in each of its three positions.

There are, in position "1", two additive components to the photon flux. These are the photons which originate at the source 12 and those which emanate from the total background which lies within the whole field-of-view of detector 30. Accordingly, the spectral filter 28 will be placed close enough to the detector that it will fill the detector field-of-view, and thus will be by far the major source of background radiation. The background contribution passing through the spectral filter can only contribute to the total background within the latter's passband, and this contribution can be shown to be negligible if the temperature of this background is below, say, 400°K. If the photon flux from the filter background is called $N_2(\lambda)$, and the photon flux on the detector due to the beam which passes through the reference cell is called $N_1(\lambda)$ (noting that this value is a function of source temperature), then there exists the relation defined as $$N_1(\lambda) = A_s \; \frac{N_s(\lambda)}{r^2} T_B(\lambda) T_F(\lambda) T_{OB}(\lambda),$$

where:

$A_s$ = projected area of the source (cm$^2$);

$N_s(\lambda)$ = number of photons emanating from the source per unit source area per second per micron per steradian (cm$^{-2}$ sec$^{-1}$ $\mu^{-1}$ster$^{-1}$);

$r$ = optical path length from source to detector (cm)

$$\frac{I_{s1}-I_{s3}}{I_{s1}-I_{s2}} = [qA_d \left\{ \int_\lambda n(\lambda)N_2(\lambda)d\lambda + \frac{A_s}{r^2}[n(\tilde{\lambda})N_s(\tilde{\lambda})T_B(\tilde{\lambda})T_F(\tilde{\lambda})T_0(\tilde{\lambda})\Delta\lambda] - \int_\lambda n(\lambda)N_2(\lambda)d\lambda \right.$$
$$\left. - \frac{A_s}{r^2}[n(\tilde{\lambda})N_S(\tilde{\lambda})T_A(\tilde{\lambda})T_F(\tilde{\lambda})T_0(\tilde{\lambda})\Delta\lambda]\right\}]/[qA_d \left\{ \int n(\lambda)N_2(\lambda)d\lambda + \frac{A_s}{r^2}[n(\tilde{\lambda})N_s(\tilde{\lambda})T_B(\tilde{\lambda}) \right.$$
$$\left. T_F(\tilde{\lambda})T_0(\tilde{\lambda})\Delta\lambda] - \int_\lambda n(\lambda)N_2(\lambda)d\lambda \right\}]$$

$T_B(\lambda)$ is the transmission of the gas in the reference cell;

$T_F(\lambda)$ is the transmission of the spectral filter; and $T_{OB}(\lambda)$ is the optical efficiency over the reference path B.

The detector short-circuit current $I_{s1}$, for mirror position "1" is, then, $I_{s1} = qA_d \int_\lambda n(\lambda) [N_2(\lambda)+N_1(\lambda)]d\lambda$ $$= qA_d [\int_\lambda n(\lambda)N_2(\lambda)d\lambda + \int_\lambda n(\lambda)N_1(\lambda)d\lambda]$$

$$= qA_d [\int_\lambda n(\lambda)N_2(\lambda)d\lambda + \frac{A_s}{r^2} \int_\lambda n(\lambda)N_s(\lambda)T_B(\lambda)T_F(\lambda)T_{OB}(\lambda)d\lambda]$$

We assume that the spectral filter transmits only in a spectral bandwidth $\Delta\lambda$ centered at 4.6 microns, so the second integral can be closely approximated as follows:

$$\int_\lambda n(\lambda)N_S(\lambda)T_B(\lambda)T_F(\lambda)T_{OB}(\lambda)d\lambda \cong n(\tilde{\lambda})N_S(\tilde{\lambda})T_B(\tilde{\lambda})T_F(\tilde{\lambda})T_{OB}(\tilde{\lambda})\Delta\lambda.$$

where $\tilde{\lambda} = 4.6\ \mu$
So, $$I_{s1} = qA_d \left\{ \int_\lambda n(\lambda)N_2(\lambda)d\lambda + \frac{A_s}{r^2}[n(\tilde{\lambda})N_S(\tilde{\lambda})T_B(\tilde{\lambda})T_F(\tilde{\lambda})T_{OB}(\tilde{\lambda}) \Delta\lambda]\right\}$$

Since in its position "2" the movable mirror will not allow photons from source 12 to reach the detector 30, the only contributor to the photon flux upon the detector is the background. Thus the detector short-circuit current $I_{s2}$, for mirror position "2", is, then, $$I_{s2} = qA_d \int_\lambda n(\lambda)N_2(\lambda)d\lambda.$$

The analysis for mirror position "3" is analogous to that for mirror position "1". The detector short-circuit current $I_{s3}$, for mirror position "3" is $$I_{s3} = qA_d \left\{ \int_\lambda n(\lambda)N_2(\lambda)d\lambda + \frac{A_s}{r^2}[n(\tilde{\lambda})N_S(\tilde{\lambda})T_A(\tilde{\lambda})T_F(\tilde{\lambda})T_{OA}(\tilde{\lambda})\Delta\lambda]\right\}$$

where: $T_A(\tilde{\lambda})$ is the transmission of the gas in the sample cell 15, and $T_{OA}(\tilde{\lambda})$ is the nominal optical efficiency over the sample path A at wavelength $\tilde{\lambda}$.

The optical path length, $r$, for the two cases will be made to be the same. If the optical efficiency $T_{OA}(\lambda)$, over path A is the same as $T_{OB}(\lambda)$, $$T_0(\tilde{\lambda}) = T_{OA}(\tilde{\lambda}) = T_{OB}(\tilde{\lambda}).$$

It will now be shown what algebraic manipulation is necessary, using $I_{s1}$, $I_{s2}$ and $I_{s3}$, in order to obtain the desired result. Later it will be shown how this manipulation can be accomplished electrically.

Or, simplifying and cancelling, $$\frac{I_{s1}-I_{s3}}{I_{s1}-I_{s2}} = \frac{T_B(\tilde{\lambda})-T_A(\tilde{\lambda})}{T_B(\tilde{\lambda})}\ \text{percent absorption}.$$

It is especially to be noted that this result is independent of source temperature, source size, detector quantum efficiency and detector size. Proceeding, in order to obtain percent transmission electronically, we must evaluate the quantity $$\frac{I_{s1}-I_{s3}}{I_{s1}-I_{s2}}$$

electronically. For this purpose we use a current-mode amplifier (D.C. feedback amplifier) as the first stage of the A.C. amplifier 32 shown in FIG. 1 (the amplifier being hereinafter described in reference to FIG. 9), so the output voltage of the A.C. amplifier will be proportional to input short-circuit current minus a D.C. offset voltage. That is, $$V_{s1} = kI_{s1} - C$$

$$V_{s2} = kI_{s2} - C$$

$$V_{s3} = kI_{s3} - C$$

where $V_{s1}$, $V_{s2}$ and $V_{s3}$ are the A.C. amplifier output voltages, $k$ is associated with the A.C. amplifier gain, and $C$ is the D.C. voltage offset.

The time relation between the movable mirror positions and the output of amplifier 32 is shown in FIG. 4. The output voltages $V_{s1}$, $V_{s2}$ and $V_{s3}$ of FIG. 5 are extracted by synchronous sample and hold circuits 46, 47 and 48, respectively, of FIG. 7, which are later described. Difference voltages $V_{s1}-V_{s2}$ and $V_{s1}-V_{s3}$, as illustrated in FIG. 6, are then extracted, and the ratio $(V_{s1}-V_{s3})/(V_{s1}-V_{s2})$ is obtained electrically. The resulting ratio is equal to the quantity $$\frac{I_{s1}-I_{s3}}{I_{s1}-I_{s2}}$$

as shown below, which is the desired result. That is, $$\frac{V_{s1}-V_{s3}}{V_{s1}-V_{s2}} = \frac{(kI_{s1}-C)-(kI_{s3}-C)}{(kI_{s1}-C)-(kI_{s2}-C)} = \frac{I_{s1}-I_{s3}}{I_{s1}-I_{s2}}$$

The above relation is interpreted to show the result is independent of A.C. amplifier gain, as manifested in k.

FIG. 7 is a block diagram of the electronic processing system 33 of FIG. 1, in which three like sub-networks 34, 35 and 36 are embodied. Each comprises one standard photo transistor and one bipolar transistor in a switching mode. Together the transistors transmit unblanking sync pulses which tell the respective synchronous sample-and-hold device 46, 47 and 48 when to sample the A.C. amplifier video output to obtain the voltages $V_{s1}$, $V_{s2}$ and $V_{s3}$ and maintain them until they are resampled at a later time.

Signals from the synchronous sample-and-hold units 46, 47 and 48, go in the way shown in FIG. 7 to differencing amplifiers 49 and 50 of a known type, in the former of which the voltage $V_{s1}$ has subtracted from it the voltage $V_{s2}$. In the amplifier 50 the voltage $V_{s1}$ has subtracted from it the voltage $V_{s3}$. The two resulting voltages now go into the divider circuit such as described in detail in FIG. 15, and, hereinafter. A video signal is presented graphically and as the output of the A.C. amplifier 32. Each of the three dual sync and synchronous sample-and-hold devices 34–46, 35–47 and 36–48 discriminates in real time each of the output signals $V_{s1}$, $V_{s2}$ and $V_{s3}$, the sync pulses having a fixed time relation to the A.C. video signal; and a function of each synchronous sample and hold, in conjunction with its sync generator, is to extract the value of the voltage of the A.C. amplifier output signal at such time that the sync signal dictates. The outputs of the synchronous sample and hold circuits are represented graphically as functions of time in FIG. 7 (as may be compared with the graph of FIG. 5), these graphical representations being located adjacent the synchronous sample and hold circuits 46, 47 and 48. The respective units 46, 47 and 48 of the latter can be sample/hold modules marketed by Burr-Brown, preferably Model 1666/16 or 4013/25. The output voltages of the subtraction devices 49 and 50 are presented graphically, as functions of time, directly following these units. The latter effectively perform the function of subtraction; however, there are a number of other known ways to subtract electrically, hence the invention should not be considered unduly limited in this regard. All of the subtractive functions described in reference to FIG. 7 can be performed by differential input operational amplifiers.

The foregoing calculations, divider, amplifier and processing circuitry enable one to obtain percent absorption as an electrical output. This output then drives the meter 38 having a non-linear scale, being calibrated in percent CO by volume at standard temperature and pressure. It may be noted that in the two-path configuration, the function of the divider of FIG. 7 can be eliminated by sampling the reference voltage and operating a source temperature controller from that voltage to maintain the reference voltage at unity, i.e., a feedback system.

The subtractive and divisive electrical values discussed above, and graphically and otherwise depicted in FIGS. 2 through 8, are derived in theory in reference to a system 10 such as is shown in FIG. 1, i.e., a system utilizing separate sample and reference energy paths 17 from emissive source 12 onto the detector 30. One skilled in the art will readily understand where the assumptions made and conclusions reached are equally valid in respect to a system of the nature hereinafter described in which but a single path of energy originating at source 12 is employed. In such an alternate system appropriate filter and/or chopper means may serve to (a) spectrally filter at the sample characteristic wavelength the energy impinging on detector 30; (b) afford a comparison background energy impinging on the detector, such as might be represented by zero or minimal energy in an operational phase corresponding to position "2" in FIG. 2; and (c) give reference energy impinging on the detector, which unlike that traversing path 17 through reference cell 16 of FIG. 1, will be of another known wavelength other than that of the gaseous constituent (CO) of the sample under analysis. It is intended that the gaseous mixture in the sample cell will have negligible absorption at this wavelength. Furthermore, under the broad principle of the invention, it is contemplated that the analysis may be in regard to a fluid other than a gas, and, indeed, to a radiant energy analysis other then infrared. Applications in the analysis of gases other than carbon monoxide have been mentioned above. Furthermore, it is contemplated that the principle of the invention may well be extended to the more-or-less simultaneous spectral analyses of a medium in respect to more than one constituent, as will appear.

One system alternative to that of FIG. 1 which will provide the same electrical output, but utilizing a single path of energy transmission through the sample medium is shown in FIG. 8. It has several advantages over the system of FIG. 1. This system, generally designated 70, has a number of components in common with the first, which are therefore designated by the same reference numberals. In addition to source, sample cell, detector and amplification-sync-processing electronic means like those of FIGS. 1 and 7–9, the system utilizes a rotary filter and chopper wheel or disc 71, driven by an appropriate means (not shown); and features of the wheel are shown in alternate embodiments in FIGS. 9 and 10. Each of two optical filters 72, 73 of the wheel occupies a substantial radial and circumferential segment area of wheel, such filter segments being more-or-less widely spaced from one another at 74; and the remaining segment 75 is opaque.

Figure 17:
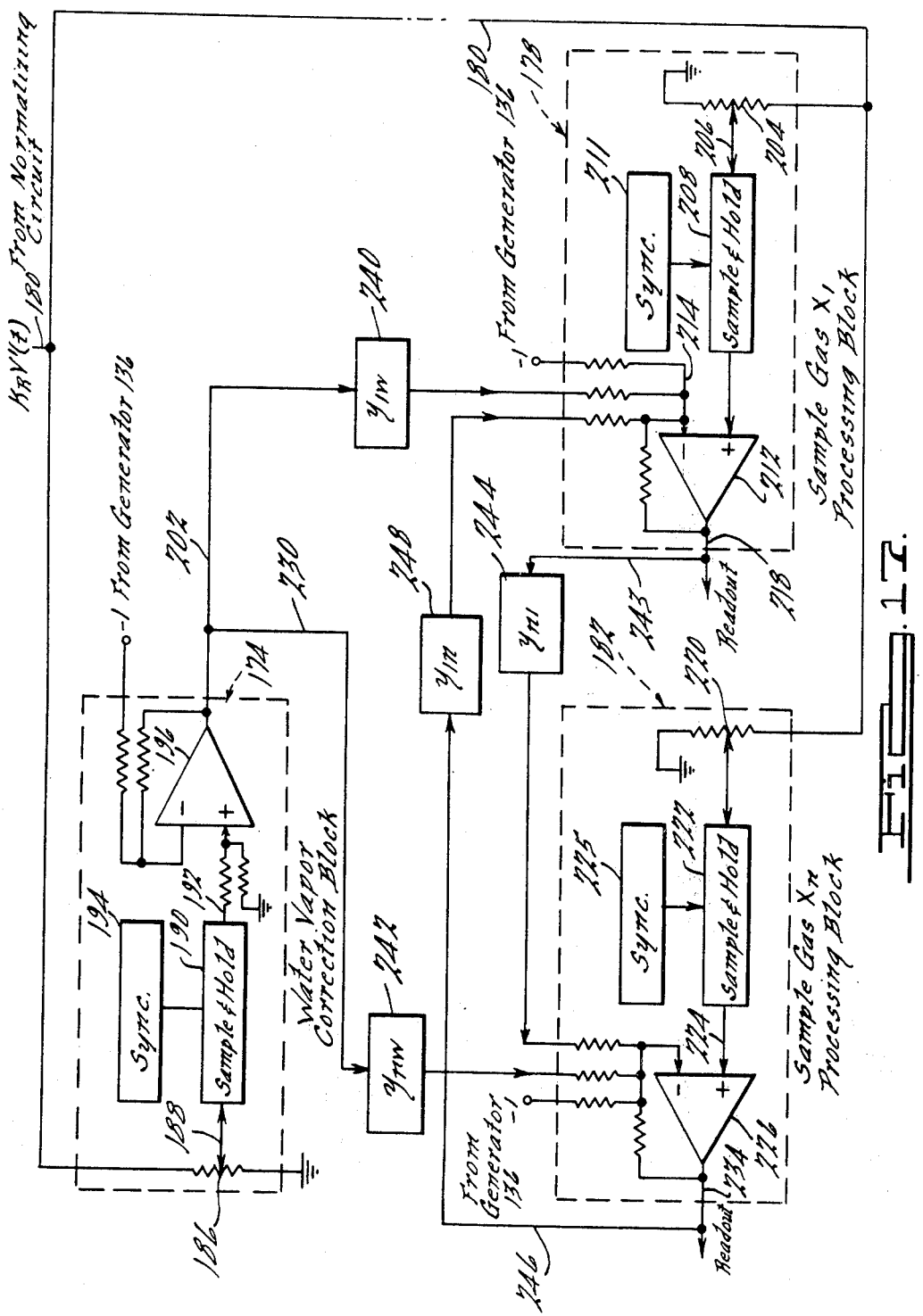
FIGS. 17 and 18 are schematic diagrams, each of which illustrates a method and structure for compensating for spectrum interferences between the gaseous components of a sample.
Figure 18:
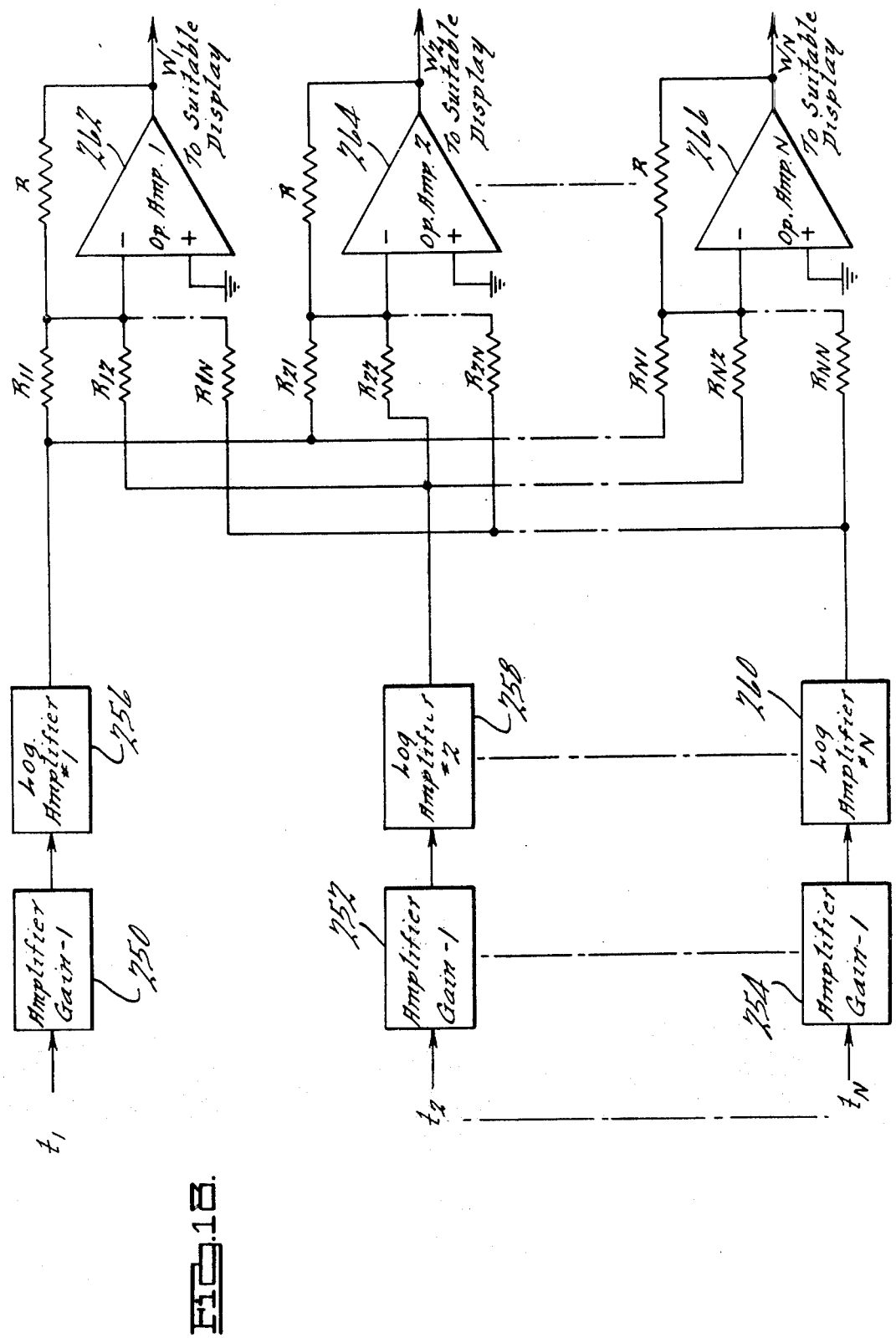

In an instance in which it is proposed to analyze two or more different gaseous constituents of a sample in one cycle of operation, the filter-chopper 71 may be modified as shown in FIG. 12 to provide still another optical filter segment at 76, in which case the amplifier, detector, electrical processing and metering arrangements will be appropriately modified in specific respects, but not essentially altering the inventive principle as put in effect by the systems of FIGS. 7, 8, and 9, as described in detail in FIGS. 17–18. Sync holes 77 in wheel 71 admit visible light to trigger photoelectrically the sync devices of system 70. Still further modifications to the filter-chopper may be made. For example, in FIG. 11, a filter-chopper 80 is illustrated having a filter window 82 which extends for approximately 180° of the filter-chopper disc. The filter window is essentially a narrow bandpass filter whose band center varies continuously as a function of angular position between the radially extending ends of the window 82. Similar to the previous embodiments of filter-choppers, synchronization holes 77 are angularly positioned along the window 82 in a predetermined fashion so as to provide pre-selected wavelength bandpasses. Accordingly, since the preselected wavelength desired for optical processing may not be evenly spaced, as depicted, the synchronization holes 77 may not be evenly spaced. As can be seen in FIG. 11, one synchronizing hole 77 is provided in a source blocking region to provide a background signal. The instantaneous effective spectral bandpass of the filter is dictated by a beam-limiting aperture. The filter aperture can be controlled in any suitable manner, for example, by incorporating a radiation block having a slit corresponding to a narrow sector of the window 82 or by using a detector of limited area.

In FIGS. 12 and 13, a preferred scheme for synchronizing a filter-chopper is illustrated. In FIG. 12, a chopper wheel 84 is illustrated having three circular filters 76, 72 and 73 which correspond to the previously described filters with the same numerical designation, and a source blocking portion. The filter wheel 84 has synchronizing openings 77 located at radially distinct positions. In FIG. 13, the filter-chopper 84 is seen to be associated with a radially-elongated light source 86 and a plurality of photocells 88 which correspond in number and radial position to the synchronizer openings 77. The location of a synchronizing hole 77 on an axis between the light source 86 and one of the photocells 88 unambiguously determines the angular position of the filter-chopper 84 with respect to the transmission path of the infrared energy from the source 12 to the detector 30.

In FIG. 14, another alternative filter-chopper assembly 90 is illustrated. The assembly 90 includes a filter-wheel 92, having filters 76, 72, 73, 94 and 96, which is directly mounted on a drive shaft 98 of a motor 100 for rotation therewith, and a chopper wheel 102 which is mounted to the drive shaft 98 through a 2 to 1 reduction drive unit 104 so that the chopper segment 102 is interposed in the path between the source 12 and the detector 30 during every other rotation of the main shaft 98. Accordingly, the background level of radiation can be obtained for each filter 72, 73, 76, 94 and 96 on every other rotation of the shaft 98 when the chopper segment 102 is positioned to block the transmission of the infrared energy from the source 12 to the detector 30 using the synchronizing system for the respective filters 72, 73, 76, 94 and 96. To this end, the detector should be positioned proximate to the filter wheel 92. It will also be appreciated that the chopper 102 and the filter wheel 92 may be mounted in remote locations and may be driven from separate sources, with the limitation that appropriate synchronization must be accomplished therebetween. Essentially any position intermediate the detector 12 and the source 30 is suitable for each of the filter wheels 92 and the chopper 102.

With reference again to FIG. 8, the theory of operation the single path system 70 is as follows: Each of the spectral or optical filters has a bandpass of approximately 0.1 micron. One of these filters, for example, filter 72, is centered at 4.6 microns. The other filter 73 is centered on a wavelength at which the gas sample mixture has virtually no spectral absorption, for example, 3.9 microns. Let the situation in which the filter 73 is in front of the detector 30 be analogous to mirror position "1" in the basic system. Likewise, let the situation in which the opaque section 75 is in front of the detector be analogous to mirror position "2", and the remaining time when filter 72 is in front of the detector be analogous to mirror position "3".

Within this correspondence, the sync-time relations of FIG. 3 apply, as will the signal-time relations of FIGS. 4-6. With no more than a gain adjustment in one of the operational amplifiers, the same sync-amplifier processing electronics as proposed in FIGS. 7-9 for the system 10 will accept the detector signal as input to provide an electrical output proportional to percent absorption.

The major advantage of the one path, two-filter system 70 over the two path, single filter system 10 of FIG. 1 is that the optical path over which the reference beam travels is identical to the optical path traveled by the sample beam. This means that if the transmission of the optical path 17 changes because of the accumulation of dirt, dust, etc., both the signal transmitted by filter 72 and the signal transmitted by filter 73 will be attenuated. Since most contaminants will affect both wavelengths to the same degree, the accuracy of the measurement will not be influenced. It should be noted that the previous assumption of equal optical efficiencies $T_{OA}(\lambda)$ and $T_{OB}(\lambda)$ over the sample and reference paths respectively is automatically realized within this configuration. However, the source photon flux $N_s(\lambda)$ through the reference and sample filters will not maintain a constant relationship to one another with changes in the source temperature. It has been found that the errors introduced with changes in source temperature are small. Additionally, the detector quantum efficiencies $n(\lambda)$ at all wavelengths utilized are not necessarily equal, but they do maintain a constant relationship to one another so as to allow a correction for variations in efficiency.

Figure 15:
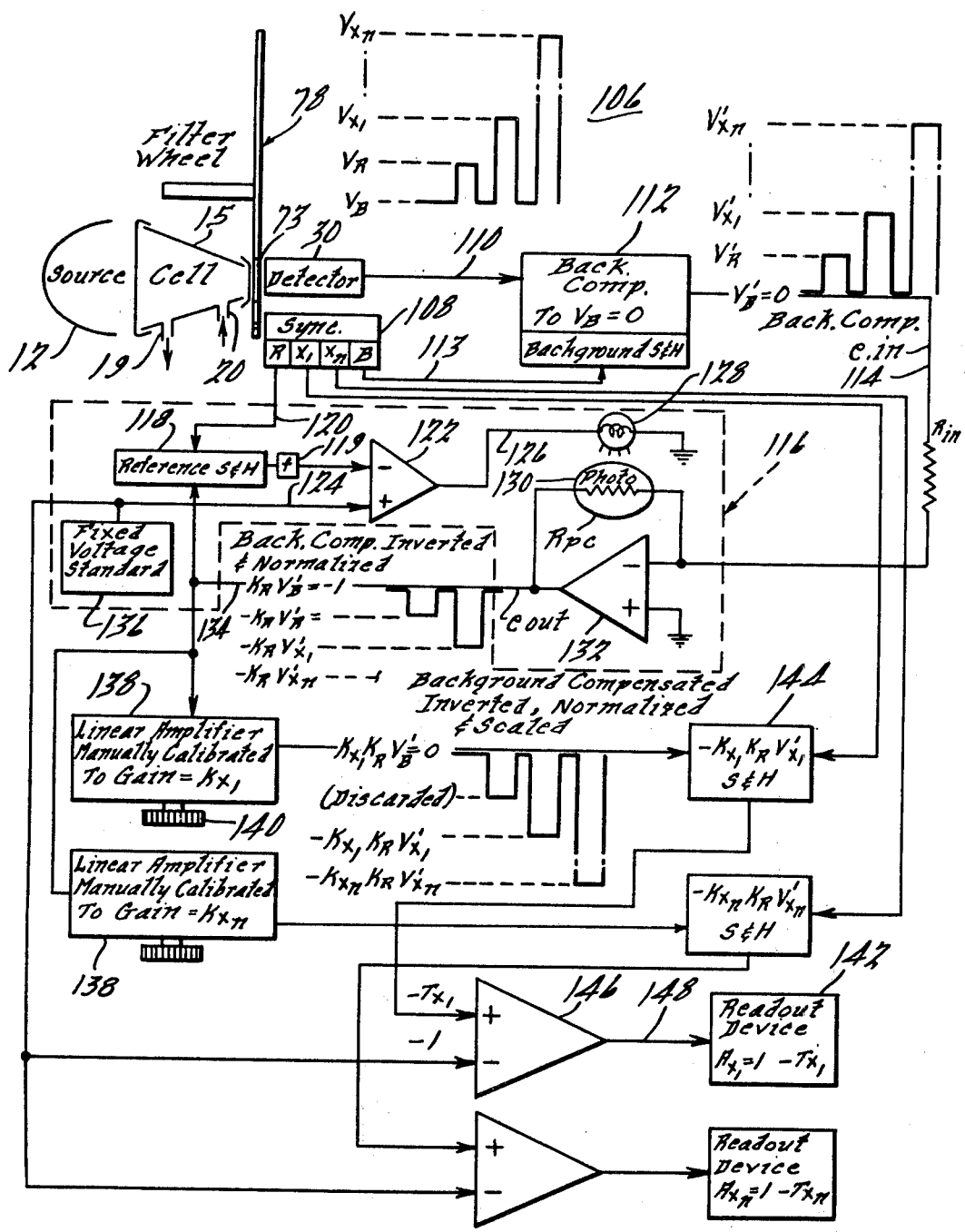
FIG. 15 is a schematic diagram of a processing circuit which may be employed with the embodiment of FIG. 8.

In FIG. 15, a schematic diagram of a single path infrared analyzer 106 is shown which is especially suitable for determining the concentrations of more than one gaseous component of a gaseous mixture. The system 106 of FIG. 15 includes a source 12, a cell 15 for containing the gaseous mixture to be analyzed having inlet passages and outlet passages 19 and 20, respectively, a filter wheel 78 which preferably is essentially as described with respect to FIG. 12 and has a plurality of filters mounted for interposition between the source 12 and the detector 30. The system 106 further includes a synchronization system 108, for example, like that disclosed in FIG. 13. The detector 30 provides an output signal on a line 110 which includes signal components $V_{X1} \ldots V_{Xn}$ $V_R$ and $V_B$ as illustrated above line 110. A background compensating or zero clamping circuit 112, connected by a suitable synchronization line 113 to the background signal indicator of the sync circuit 108, is provided which includes a sample-and-hold circuit for storing the signal $V_B$ for subtraction from each of the signals $V_R$, $V_{X1} \ldots V_{Xn}$ to provide zero clamped, background compensated, signals $V'_R$, $V'_{X1} \ldots V'_{Xn}$, respectively, on the output line 114 of the zero clamping circuit 112. The signals on output line 114 are normalized by an analog divider 116 which divides the background compensated signals on line 114 by a signal representative of the background compensated reference signal $V'_R$ obtained when the reference filter 73 is interposed in the path between source 12 and the detector 30.

The divider circuit 116 includes a sample-and-hold circuit 118, a filter 119, a control differential amplifier 122, a variable resistance device which in this instance comprises a light source 128 and an associated photosensitive device 130, a main differential operational amplifier 132, and a fixed voltage standard generator 136. It is the object of the voltage divider circuit 116 to divide each incoming signal by the negative of the background compensated reference voltage $-V'_R$, when the divider is in a steady-state (non-transient) condition. In other words, the divider circuit 116 multiplies the incoming signal train by a quantity $-1/V'_R$, which may be arbitrarily said to equal the quantity $-K_R$, where $K_R = 1/V'_R$. The signal out of the divider 116 on an output line 134 is considered to be "normalized". Obviously, in a steady-state condition, the normalized, background compensated reference signal $-K'_R \cdot V'_R = -1$. To fully appreciate the operation of the analog divider 116, consider the main operational amplifier 132 connected in a simple inverting configuration as shown with the gain $e_{out}/e_{in}$ of the operational amplifier being essentially equal to $-R_{PC}/R_{in}$ when $R_{in}$ is the input resistance to the amplifier 132. The output of the main operational amplifier 132 is applied to the sample-and-hold unit 118 whose aperture time is controlled by the reference sync circuit 108. The sample-and-hold unit 118, then, samples the reference level within the output of the main operational amplifier 132 every time the reference sync pulse occurs and maintains this level on its output. The output of the sample-and-hold unit 118 is applied through a low pass filter 119 to the inverting input of the control differential amplifier 122. The standard voltage signal on line 124 from the generator 136, which is set to be a value $-K_1$ volts which value is arbitrarily considered to be negative "one", is applied to the noninverting input terminal of the differential amplifier 122. Accordingly, whenever the reference level within the output of the operational amplifier 122 deviates from $-K_1$ volts, an error signal is generated at the output of the control differential amplifier 122 on line 126. The error signal on line 126 is applied to the control terminal of the voltage-controlled resistance element, in this case, the light source 128 thereof. The value of the resistance $R_{PC}$ of the associated photosensitive device 128 and thus the closedloop gain of the operational amplifier 132, changes in accordance with the intensity of light emitted from the light source 128 so as to nearly restore the $e_{out}$ reference level of the output of the main operational amplifier 132 to the value $-K_1$. For example, when a difference exists between the background compensated, reference signal from the main operational amplifier 132 and the signal assumed negative "one" from the fixed voltage standard generator 136 a signal is provided on line 126 which is proportional to the difference in the signals. Accordingly, the intensity of the light 128 will be a function of the difference so as to correspondingly decrease the photocell resistance $R_{PC}$ of the photocell 130 so as to adjust the feedback resistance in a manner to make more positive the output voltage $e_{out}$ of the main operational amplifier 132 when the background compensated reference signal $V'_R$ is more negative then negative "one" or to make more negative the output voltage $e_{out}$ of the main operational amplifier 132 by increasing the photocell resistance $R_{PC}$ when the background compensated reference signal $V'_R$ is more positive than the assumed signal value of negative "one" so as to maintain the relationship $e_{out} = -K_R e_{in}$.

The system shown in the diagram may specifically operate in either of two manners. In the first of the two manners of operation, the restoration process occurs entirely within a time period which corresponds to the pulse width of a single reference sync pulse. No further restoration occurs between sync pulses. Control theory would generally state that if this system were to be stable, the response time of the sample-and-hold unit 118, the control differential amplifier 122 and the voltage-controlled resistance 128 and 130 would have to be short with respect to the reference pulse width. In this case, no low pass filter 119 would be used. When one is utilizing a very high filter wheel rotational rate, as in the case in the preferred gas analyzer according to this invention, the reference sync pulse width can be quite small (100 microseconds). The sample-and-hold unit 118 as well as the control differential amplifier 122 can be made to respond much more quickly than this, but it is difficult to obtain a voltage-controlled resistance unit which responds this quickly. Field-effect transistors may be used as voltage-controlled resistors and will respond this quickly, but they behave as almost pure resistors from drain-to-source only at very small drain-to-source voltages. Phototransistors or photodiodes used with light-emitting diodes as specifically disclosed herein, will also respond quickly but they behave as almost pure resistors only under some specialized conditions. This first described mode of operation, is, then, rather difficult to achieve.

A second of the two manners of operation is preferred in this application. In this second manner of operation, the restoration process takes place almost continuously, based upon a comparison of the reference level and the output of the operational amplifier 122 which is obtained by low-pass filtering the output of the sample-and-hold unit 118 by any suitable, known filter 119. The comparison, in essence, results in a weighted average of many discrete sample-and-hold outputs. Thus, the restoration rate will be relatively slow with respect to the period of rotation of the filter wheel. It must be relatively slow in order to achieve a stable system. The speed of restoration is determined by the restoration accuracy desired. Control theory generally says that any desired restoration accuracy may be obtained, but that the higher the restoration accuracy is, the slower must be the restoration rate if the system is to remain stable.

It can be seen in FIG. 15 that the signals representative of the respective ones of the gaseous components of the gaseous mixture are sequentially received by the analog divider 116 for conversion and normalization through division by the reference signal $-V'_R$ to produce zero clamped, inverted and normalized signals $-K_R V'_{x_1} \ldots -K_R V'_{x_n}$. Accordingly, the analog divider 116 is time shared to accommodate any desired number of component signals. All of the component signals are sent to respective linear amplifiers, a first being shown at 138 for component signal $-K_R V'_{x_1}$. The linear amplifier 138 may be calibrated either manually as by an appropriate adjustment knob 140 or may be automatically calibrated, for example, by a digital zeroing circuit or other automatic control. It will be appreciated that an additional linear amplifier 138 is provided to process each signal corresponding to a gaseous component under investigation. For example, an additional linear amplifier 138 is illustrated for the generalized case of a gaseous compound $X_n$.

With clean air in the sample cell 15, the gain of the linear amplifier 138 is adjusted so that the output at a readout device 142 for that component is zero. More particularly, the linear amplifier 138 multiplies the zero clamped, normalized and inverted signal $-K_R V'(t)$ by a constant $K_{X1}$ determined by the calibrating procedure so that an output signal $-K_{X1} K_R V'(t)$ is provided.

So that each signal representative of respective ones of the gaseous components may be individually read out, signal discrimination must be provided. Signal discrimination is conveniently accomplished by utilizing a sample-and-hold circuit 144 which receives the output signal of the linear amplifier 138 and at appropriate times, as determined by the synchronizing circuit 108, stores that signal for continuous delivery to the additive terminal of an amplifier 146 while the fixed voltage standard from the negative "one" generator 136 is supplied to the subtractive terminal of the operational amplifier 146 to subtract a signal of negative "one" from the quantity $-K_{X1}K_RV'_{X1}$. Accordingly, when clean air is in the sample cell 15, the operational amplifier 146 will yield an output signal of "zero" on an output line 148 which is connected to the readout device 142. When a gaseous mixture to be analyzed contains a concentration of a component $X_1$ which is above the calibration air concentration, the signal $-K_XK_RV'_{X1}$ will be more positive than negative "one" so as to provide a positive signal $A_{X_1}$ at the readout device 142. As previously formulated, the indication $A_{X_1}$, of the readout device 142 will be representative of the concentration of the gaseous component $X_1$ in the gaseous mixture within the cell 15. An identical process is conducted to determine the concentration signal $A_{Xn}$ for the gaseous component $X_n$ as illustrated in FIG. 15.

In view of the above explanation, it can be seen that each corresponding linear amplifiers 138, sample-and-hold circuits 144 and operational amplifiers 146 for respective ones of the gaseous components to be investigated are connected to respective ones of the readout devices 142, only one of which is numbered in FIG. 15, so that the concentration of the other gaseous components will be determined in sequence as the filter for that component is interposed in the path between the source 12 and the detector 30.

Figure 16:
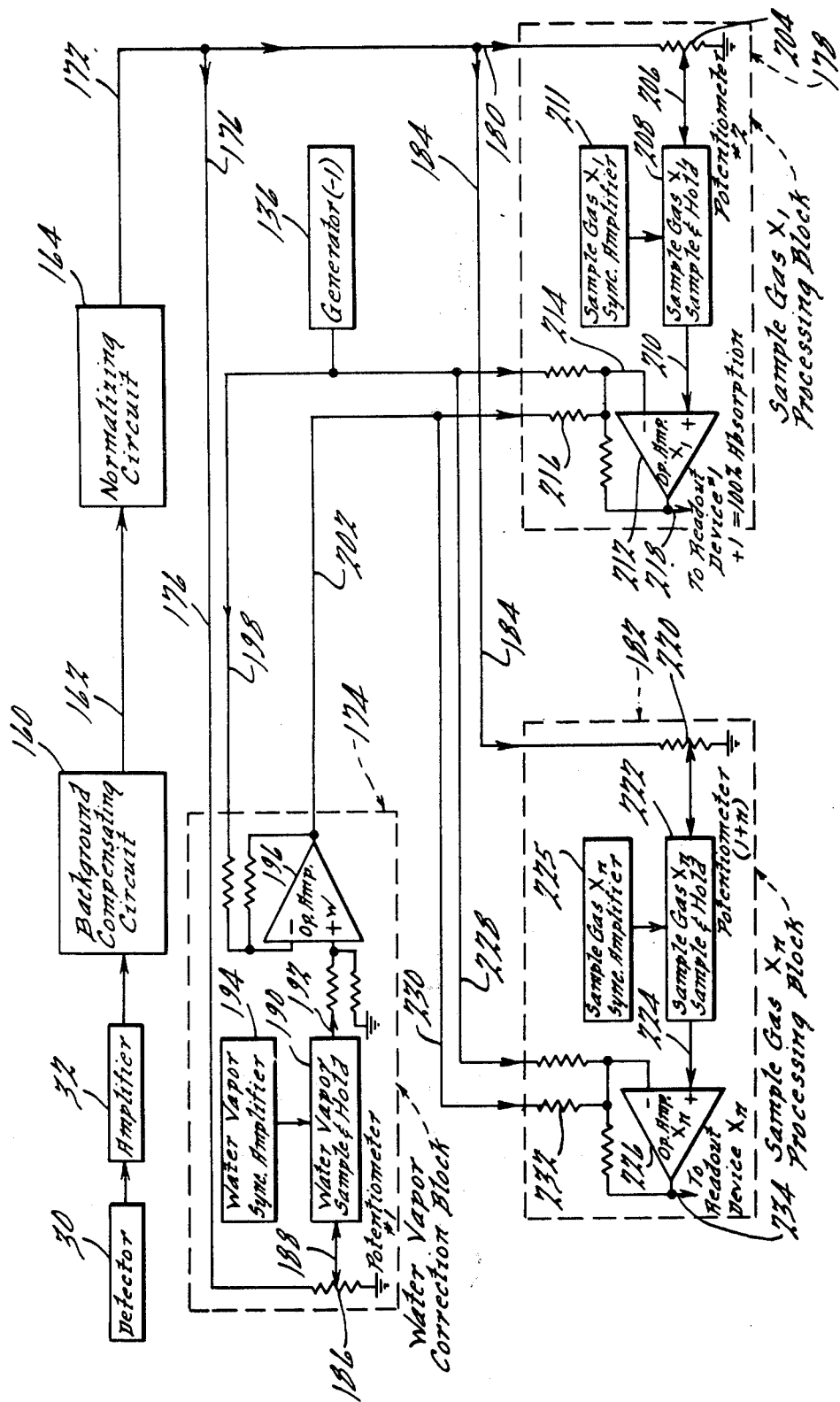
FIG. 16 is another schematic diagram of a processing circuit which provides water vapor interference compensation and which may be employed with the embodiment of FIG. 8.

In FIG. 16, a schematic diagram is shown of another embodiment of analyzer processing circuitry which includes a provision for electrically compensating for absorption band interferences. Although this embodiment will be particularly described with respect to compensation for absorption band interferences of water vapor concentrations in the gaseous mixture, it will be appreciated that the principles stated herein are equally applicable to the compensation of other interfering gaseous components as will be described in greater detail hereinafter.

The problem solved by the absorption band interferences compensation circuitry of FIG. 16 can be better appreciated if the desired performance of a fully versatile automobile exhaust analyzer is considered. The analyzer should measure the concentrations of four gases: carbon monoxide, carbon dioxide, hydrocarbons, and the oxides of nitrogen. It has been found that the absorption spectra of several of these gases overlap with each other and other gaseous components of the gaseous mixture so that, as a practical matter, it is not always possible to select a wavelength at which there is sizable infrared absorption by one of the gaseous components under investigation, but no significant infrared absorption by any of the others, i.e. no absorption band interference. Accordingly, the absorption spectra of the various gases must be analyzed to determine the degree of interference and such interference should be corrected when a significant interference occurs so as to provide a desired high level of measurement accuracy. For example, water vapor is found in automobile exhausts and is not normally a subject for emission control; and accordingly, the concentration of water vapor is not normally measured. However, water vapor provides a significant infrared absorption contribution at any of the wavelengths at which the oxides of nitrogen have a significant infrared absorption, i.e. the nitric oxide absorption band is overlapped by a strong water vapor absorption band. Moreover, the hydrocarbon fundamental absorption band, centered at a wavelength of 3.4 microns, is on the fringes of a strong water vapor absorption band. The prior art methods for dealing with the water vapor problem, e.g. the removal of all of the water vapor from the sample before it enters the sample cell by a dryer, or the use of a gaseous saturation filter, have been found to be inconvenient or ineffective in use and require maintenance procedures which are often neglected so that measurement accuracy is not reliably achieved in the field. The method and structure of the present invention electrically compensates for absorption spectrum overlapping and presents none of the operational drawbacks associated with the prior art devices.

With reference now to FIG. 16, the electrical processing circuit which provides appropriate water vapor compensation is illustrated. In FIG. 16, the aforementioned detector 30 is used to provide the various previously described background, reference and component signals $V_B$, $V_R$ and $V_{X_1}...V_{X_n}$, respectively, which are amplified by an amplifier 32. The processing electronics of FIG. 16 are preferably incorporated within a system as described with respect to FIG. 15 which has a filter wheel 78 with a plurality of the necessary filters, i.e. a filter for providing the reference signal $V_R$ and a filter for providing a component signal $V_{X_1}...V_{X_n}$ for each of the components under investigation. Also, a source chopper or source blocking means is incorporated for the measurement of the background level of radiation. The filter wheel 78 and the source chopper are associated with a synchronizing device 108 which provides synchronizing signals by synchronizing amplifiers to control the storing of the various signals in respective sample-and-hold circuits as previously described. It can be seen that the circuitry of FIG. 16 incorporates a background compensation circuit 160, disclosed in FIG. 15, which receives the output signals from the detector amplifier 32 and subtracts a signal representative of the level of the background radiation from each of the signals of the incoming signal train to yield a train of background compensated signals on output line 162. The signals on line 162 arrive at a normalization circuit 164 also as taught with respect to FIG. 15, which divides the incoming signals by the reference level of radiation to provide background-compensated, normalized output signals $-K_RV'(t)$ on an output line having time-spaced components which correspond to each of the gaseous components under investigation. It can be seen that the signal $-K_RV'(t)$ on output line 172 is delivered to a water vapor correction block 174 via a line 176, a sample gas $X_1$ processing block 178 via line 180, and a sample gas $X_n$ processing block 182 via a line 184.

A gain $K \geq 1$ may be applied to the signal $-K_RV'(t)$ out of the normalization circuit where K is of sufficient magnitude that the variable gain amplifiers, (for example 138 of FIG. 15) may be replaced by simple potentiometers 186, 220 and 204 of FIG. 16. That is, n variable gain amplifiers are effectively replaced by the combination of the applied gain K and the attenuation capability of the potentiometers. Thus the constant K can be absorbed into the constants $K_W$, $K_{X1}$, $K_{X2}$, ..., $K_{Xn}$ without loss of generality.

It can be seen that the signal $K_R V'(t)$ on line 176 is connected to one terminal of a water vapor calibration potentiometer 186 which may be adjusted to multiply the voltage on line 176 by the factor $K_W$. The voltage so multiplied appears on the slidable potentiometer arm 188 and is presented to the input of the water vapor sample-and-hold circuit 190 for storing therein when commanded by a water vapor sync amplifier 194. The water vapor sample-and-hold circuit 190 provides an output signal on line 192, which may be expressed as $-K_W K_R V'_W$ which is sent to the additive terminal of an operational amplifier 196. The operational amplifier 196 also receives a negative "one" signal at its subtractive input from line 198 from the negative "one" generator 136. The water vapor operational amplifier 196 provides a signal on output line 202 representative of $-K_W K_R V'_W + 1$. The output of the operational amplifier 196 is zero when there is no water vapor for the sample. The signal on output line 202 from operational amplifier 196 is thereafter used to compensate the signals of each of the gaseous components under investigation in a manner to be described hereinafter, the signal being appropriately weighed to compensate each of the gaseous components.

The line 180 of the sample gas processing block 178 is connected to a calibration variable potentiometer 204 having an output terminal 206 for zeroing the gas component $X_1$ display device with a clean air sample in the sample cell establishing the value of $K_{X1}$ as previously described. The output terminal 206 of the variable potentiometer 204 provides a signal which indicates a voltage representative of the incoming inverted background compensated, and normalized sample gas component $X_1$ signal multiplied by a gas component $X_1$ calibration constant $K_{X1}$. The signal representative of $-K_{X1} K_R V_{X1}'$ appearing at potentiometer output terminal 206 is delivered to the sample gas sample-and-hold circuit 208 so as to store the inverted, background compensated, normalized and calibrated sample gas component $X_1$ signal at the appropriate time, rejecting the remainder of $-K_{X1} K_R V'(t)$. That signal is provided to the additive terminal of operational amplifier 212 which also receives the signal representative of negative "one" from the negative one generator 136 at its subtractive input via line 214. The output signal from the water vapor operational amplifier 196 on output line 202 is also connected to the subtractive input of the operational amplifier 212 through a suitable weighting resistor 216 which modifies the amplitude of the signal in accordance with a predetermined infrared absorption contributed by water vapor at the bandpass of the filter for gaseous component $X_1$. The operational amplifier 212 subtracts the value negative "one" and the weighted water vapor compensation value from the inverted, normalized and background compensated signal $-K_R K_{X_1} V_{X_1}'$ to provide a water vapor compensated output signal appearing on output line 218 of the operational amplifier 212 which may be connected to a suitable readout device (not shown).

A processing block is provided for each gaseous component to be investigated, for example, a processing block 182 is provided for determining the concentration of a gaseous component $X_n$ having a calibration variable potentiometer 220, a sample-and-hold circuit 222 keyed by a sync amplifier 225 for delivering an inverted, calibrated background compensated and normalized signal on an output line 224 to an operational amplifier 226. The amplifier 226 also receives a negative "one" signal from the generator 136 on line 228, and a signal representative of water vapor concentration on line 230 which is weighted by a resistor 232 to yield a water vapor compensated output signal on line 234. Of course, additional processing blocks may be provided so that the concentrations of any desired number of gaseous components may be determined.

In FIG. 17, a generalized schematic diagram of a system for compensating for spectrum interference in a selected band by more than one gas. More specifically, consider a system wherein the infrared band selected for a particular gaseous component of a mixture is one in which several other components of the gaseous mixture absorb significantly so as to interfere at the selected band. To provide a highly accurate instrument, the detector signal for that particular gaseous component of the mixture must be modified so as to correct the signal error due to the interference of the other gaseous components.

Referring now specifically to the system of FIG. 17, it can be seen that many signal processing components are utilized which are essentially alike to those described with respect to FIGS. 15 and 16, and accordingly, those components have been designated with identical numbers and will not be described in detail. Among the previously described components are a water vapor correction block 174, a sample gas $X_1$ processing block 178, and a sample gas $X_n$ processing block 182. The sample gas components $X_1$ and $X_n$ processing blocks 178 and 182, respectively, are appropriately modified to receive correction signals for the other gases as well as for water vapor.

Generally describing the functioning of the circuit of FIG. 17, the output of each interfering gas processing block is connected to the subtractive terminal of the output operational amplifier of the affected gas processing block through an interference correction transfer circuit which appropriately modifies the output signal from the interfering gas processng block so as to represent an appropriate correction for the interference. More specifically, a line 202 connects the output of the water vapor differential amplifier 196 to the subtractive input of the sample gas $X_1$ output operation amplifier 212 through an interference correction transfer circuit 240. The interference correction transfer circuit 240 provides a transfer function $Y_{1w}$ which may be a non-linear function or a linear function as would be supplied by a simple resistor. The interference correction transfer circuit 240, in effect, multiplies the output signal $A_W$ of the water vapor correction block by the transfer function $Y_{1w}$ to provide an output signal from the transfer circuit representing the $A_w Y_{1w}$ which signal is effective to appropriately modify the output of the sample gas component $X_1$ processing block 178 to achieve spectrum interference compensation. In a similar manner, a line 230 is provided from the output of the water vapor correction block 174 which is connected to the subtractive terminal of the sample gas component $X_n$ output operational amplifier 226 through an interference correction transfer circuit 242 which multiplies the output signal $A_w$ from the water vapor correction block 174 by the transfer function $Y_{nW}$ to yield an appropriate correction signal $A_w Y_{nW}$ for the sample gas component $X_n$ processing block 182.

In the embodiment of FIG. 17, the output signal for sample gas component $X_1$ is compensated for spectrum interference due to the presence of a concentration of the sample gas component $X_n$ in the sample cell, and conversely, the output signal for sample gas $X_n$ is compensated for spectrum interference due to the presence of a concentration of a sample gas component $X_1$ in the sample cell. More specifically, an output line 243 of the sample gas component $X_1$ processing block 178 is connected to the subtractive terminal of the output operational amplifier 226 of the sample gas component $X_n$ processing block 182 through an interference correction transfer circuit 244 which multiplies the output signal $A_{X1}$ of the sample gas X processing block 178 by transfer function $Y_{n1}$ to provide an appropriate signal for compensating the output signal of the sample gas component $X_n$ processing block 182 for the interference caused by the concentration of sample gas component $X_1$. Conversely, an output line 246 of the sample gas component $X_n$ processing block 182 is connected to the subtractive terminal of the output operational amplifier 212 of the sample gas component $X_1$ processing block 178 through an interference correction transfer circuit 248 which multiplies the output signal $A_{Xn}$ of the sample gas $X_n$ processing block 182 by transfer function $Y_{1n}$ to provide an appropriate signal for compensating the ouput signal of the sample gas component $X_1$ processing block 178 for the interference caused by the concentration of sample gas component $X_n$.

The processing system of FIG. 17 may be zeroed by adjustment of the variable potentiometers 186, 204 and 220. Since the adjustment of each sample gas component affects the readout of the other sample gas components, the zeroing sequence is normally repeated a sufficient number of times so as to converge the output readings to zero or acceptably near zero, so that acceptably small zero reading errors are achieved. It is preferred, particularly when an increased number of sample gas components are to be measured, to generally use the zeroing procedure as follows: The zeroing potentiometer of the processing block for the gaseous component which is least influenced by, and has the greatest influence on, the other gaseous components of the mixture is preferably adjusted first so that the meter reading for that gaseous component is zero. Secondly, the potentiometer of the processing gas for the gaseous component which is next to the least influenced by, and has the next to the greatest influence on the other gaseous components, is adjusted to a zero reading on the meter. The process is repeated for each of the gases in sequence generally in accordance with the above criteria. Of course, the zeroing procedure may be varied to achieve convergence as rapidly as possible. By way of illustration, consider an automobile exhaust gas sample containing water vapor, hydrocarbons, carbon dioxide, carbon monoxide, oxides of nitrogen which is to be analyzed to determine the concentrations of hydrocarbons, carbon dioxide, carbon monoxide, and the nitrides of oxygen. General accordance with the aforementioned zeroing criteria, it is preferred to initially adjust the output signals of the carbon dioxide and water vapor processing blocks to zero since they are the least influenced by the other gaseous components and have the greatest influence on the other gaseous components. Thereafter, the processing blocks for carbon monoxide, the hydrocarbons, and the oxides of nitrogen are zeroed in sequence. After the first zeroing sequence, the sequence is repeated until sufficient zeroing convergence is attained so that the deviations of the meter readings from zero are suitably small. Of course, the manual zeroing proceeding described above can be readily implemented by digital computers through programming techniques which are well known to the art.

In FIG. 18, another circuit for compensating for spectrum interferences is illustrated. In the previous embodiment shown in FIG. 17, appropriately weighted quantities representative of the interfering contribution of each of the interfering gases are subtracted from the output signals for each of the gases. In the system of FIG. 18, a generalized scheme is disclosed wherein quantities representative of the transmittances of the mixture at selected bands are converted into logarithmic-related values, appropriately weighted, and summed to provide output signals which are representative of the concentrations of the respective gaseous components, and are compensated for spectrum interferences.

In essence, a solution to a system of simultaneous equations is obtained by the above described steps which generate the desired output signals representative of the concentration of the gases. The generation of the simultaneous equations and the manner in which the solution is obtained can be seen as follows: Let $v_1...v_N$ be distinct wavelength bands of infrared energy (relatively narrow) at which gaseous components 1, ..., N of the gaseous mixture of N gases have their principal absorptions. The transmission $t_{ij}$ in wavelength band $v_i$ ($i=1,...,N$) when a gas $j$ ($j=1, ..., N$) of concentration $w_j$ is present in an optical path is given by Beer's law to be:

$$t_{ij} = \exp[-k_{ij} w_j s]$$

where $k_{ij}$ is the normal absorption coefficient of gas $j$ in wavelength band $v_i$ and s is the length of the absorbing path. The transmission $t_i$ in wavelength band $v_i$ when the mixture of N pure gases is in the path is the product $$t_i = \prod_{j=1}^{N} t_{ij} \qquad i=1, ..., N$$

Substitution of the above equations relates the transmission $t_i$ to the individual gas concentrations, $$t_i = \exp[-s \sum_{j=1}^{N} k_{ij} w_j] \qquad i=1, ..., N$$

Taking the natural logarithm of both sides of the above yields $$\log t_i = -s \sum_{j=1}^{N} k_{ij} w_j \qquad i=1, ..., N$$

which is a system of simultaneous linear equations which may be solved by any known method. For example, let $\overline{\text{Log } t}$ denote the column vector whose elements are $\log t_i$ ($i=1,...,N$), $\overline{W}$ the column vector whose elements are the $w_j$, and $K$ to be the N-by-N matrix $[k_{ij}]$. Then the above equation can be rewritten $$\overline{\text{Log } t} = -sK\overline{W}$$

whose solution, assuming K is nonsingular, is $$W = -(1/s)K^{-1} \overline{\log t}.$$

Denote the elements of $K^{-1}$ as $c_{ji}$ $(i,j=1,...,N)$ Then the spectrum interference conpensation equation is:

$$w_j = -(1/s) \sum_{i=1}^{N} c_{ji} \log t_i, \quad j=1 ..., N$$

Consider that the only quantities needed to obtain the gas concentrations $w_1, w_2...,w_N$ are the transmission values $t_1, t_2...t_N$ in spectral bands $v_1, v_2, ... v_N$. The sample path length s appearing in the equations for $w_j$ is a known system parameter. The terms $c_{ji}$ $i=1, 2,..., N;$ $j=1, 2,..., N$, also appearing in the equations for $w_j$ can be obtained mathematically via tabulated values for the absorption coefficients $k_{ij}$.

Referring to FIG. 15, note that the signal value $-K_{X_1} K_R V'_{X_1}$ is the output of the sample-and-hold circuit 144 and that the signal values $-K_{X_N} K_R V'_{X_N}$ may be made available as outputs of similar smaple-and-hold units (not all shown). For purposes of this explanation; assume that the water vapor channel is simply one of the N gases considered. Now, further recall that $K_R=1/V'_R$, and that each constant $K_X$ is adjusted during a calibration procedure (as described hereinafter). Thus, $$-K_{X_1}K_RV'_{X_1} = -K_{X_1} \frac{V'_{X_1}}{V'_R} = -t_1$$

$$-K_{X_2}K_RV'_{X_2} = -K_{X_1} \frac{V'_{X_2}}{V'_R} = -t_2$$

$$-K_{X_N}K_RV'_{X_N} = -K_{X_N} \frac{V_{X_N}}{V'_R} = -t_N$$

1 The above signal values are, in essence, transmission values multiplied by negative unity. Using these available signal values $-t_1, -t_2, ..., -t_N$ the circuit of FIG. 18 will produce, in accordance with equation 7, the values of $w_j$ $j=1, 2, ..., N$.

Referring now to FIG. 18, the signal values $t_1, t_2,...t_N$ available from the sample-and-hold circuits of FIG. 15, as previously described, are delievered to N inverting amplifiers shown as 250, 252, and 254, respectively to multiply the incoming signals by negative one. The resulting signals are delivered to N log amplifiers shown as 256, 258, and 260 to provide logarithmically related output signals. Each of the logarithmically related output signals are connected to the subtractive terminals of each of N output operational amplifiers shown as 262, 264 and 266 through appropriate weighting resistors. For example, a signal representative log $t_1$ from log amplifier 256 is delivered to operational amplifier 262 through weighting resistor $R_{11}$, to operational amplifier 264 through weighting resistor $R_{21}$, and to operational amplifier 266 through weighting resistor $R_{N1}$; a signal representing log $t_2$ from log amplifier 58 is delivered to operational amplifier 262 through weighting resistor $R_{12}$, to operational amplifier 264 through weighting resistor $R_{N2}$; and a signal representing log $t_3$ from log amplifier 260 is delivered to the output operational amplifier 262 through weighting resistor $R_{2N}$, and to operational amplifier 266 through weighting resistor $R_{NN}$. Output signals $w_1, w_2,...w_N$ are provided by output operational amplifiers 262, 264, 266, respectively, which may drive a suitable display to provide an indication of the concentration of the gaseous components $X_1, X_2, ... X_N$, respectively.

In order to provide the appropriate concentration output signals, the values $R_{ij}$ $i=1, 2, ..., N; j=1,2, ..., N$, are made to satisfy the following relationship:

$$\frac{R}{R_{ij}} = \frac{c_{ji}}{s} i=1,2,..., N; j=1,2,..., N$$

Thus, since for $j=1,2, ..., N$ $$w_j = - \frac{R}{R_{j1}} \log [t_1] - \frac{R}{R_{j2}} \log [t_2] - ... - \frac{R}{R_{jN}} \log [t_N]$$

Then, $$w_j = - \frac{c_{j1}}{s} \log [t_1] - \frac{c_{j2}}{s} \log [t_2] - ... - \frac{c_{jN}}{s} \log [t_N]$$

The calibration procedure consists of the steps of a) placing a non-absorbing gas in the sample cell, and b) adjusting the values $K_{X_i}$ (via the potentiometers) until $$K_{X_i} \frac{V_{Xi}}{V'_R} = -1.$$

Since the non-absorbing gas in the sample cell has a transmittance of unity, the quantity $$-K_{Xi} \frac{V_{Xi}}{V'_R}$$

will now be equal to the negative of the transmittance of the gas in the sample cell. This condition is achieved when all of the outputs of the log amplifiers are zero. Once this condition has been achieved, the following equation will apply when any sample gas is placed in the sample cell:

$$w_j = - \frac{c_{j1}}{s} \log t_1 - \frac{c_{j2}}{s} \log t_2 - ... - \frac{c_{jN}}{s} \log t_N \quad j = 1,2, ..., N$$

or $$w_j = \sum_{i=1}^{N} [- \frac{c_{ji}}{s} \log t_i] \quad j=1,2 ..., N$$

or $$w_j = - \frac{1}{s} \sum_{i=1}^{N} [c_{ji} \log t_i] \quad j=1,2, ..., N$$

Thus the output signal will be obtained electronically in accordance with the spectrum interference compensation equation when the system parameters of the processing system 18 are established in accordance with the above.

In view of the foregoing, it will be appreciated that in each of the exemplary processes circuits disclosed herein, reference, background and component signals are obtained, the reference and gaseous component signal compensated for the background level of radiation by subtracting the background signal from each, and a ratio of each of the gaseous component signals with respect to the reference signal is obtained. By virtue of the foregoing signal processing, the spectrophotometer according to this invention may be set up for use, i.e. zeroed, on ordinary air and does not require zero or span gases nor does it rely upon insertion of a filter of known attenuation in the optical path as part of a calibration procedure.

Figure 19:
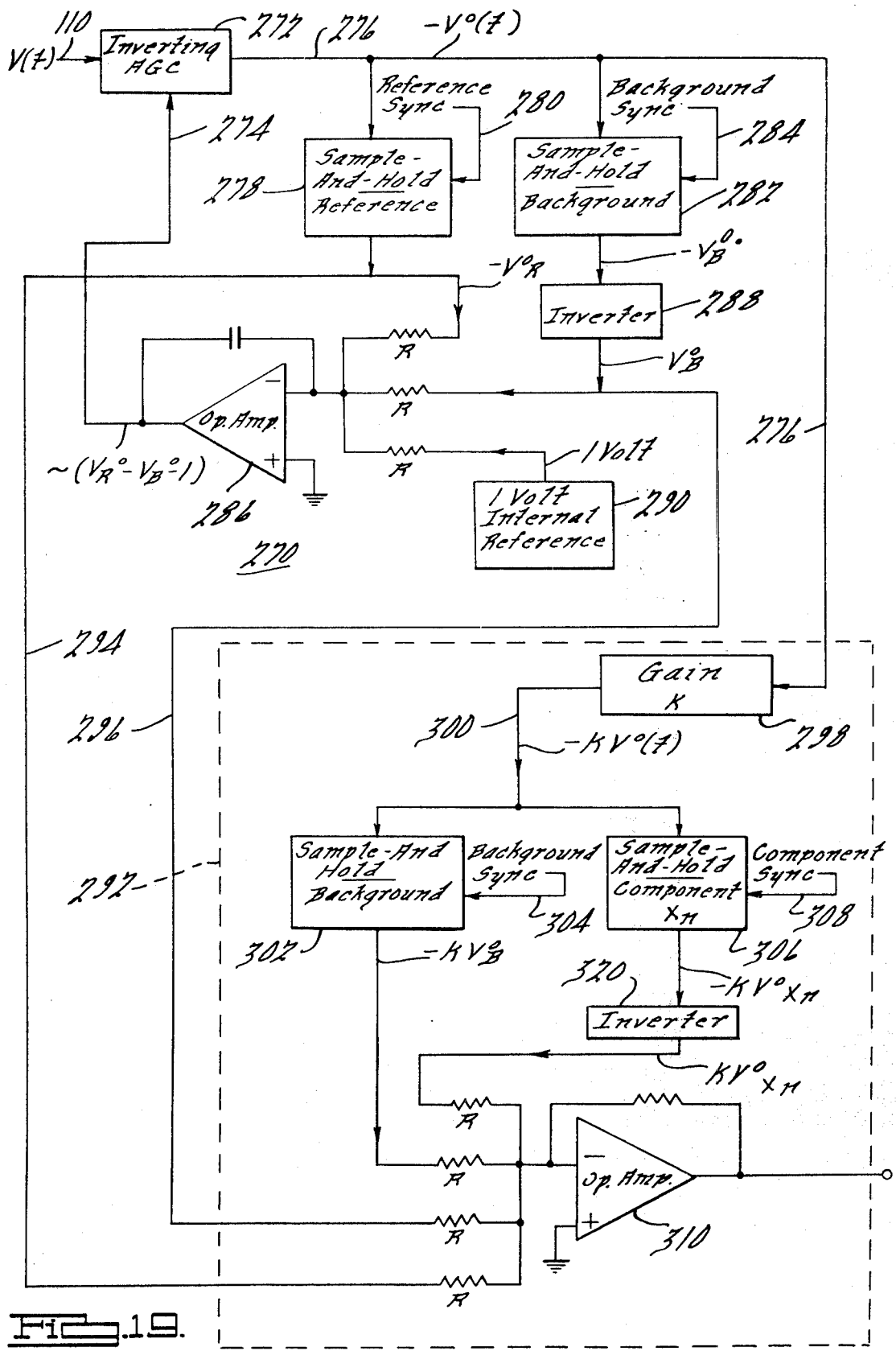
FIG. 19 is a schematic diagram of an alternative processing circuit which may be employed with the embodiment of FIG. 8.

In FIG. 19, yet another embodiment of the present invention is illustrated. In the figure, a signal processing system 270 is illustrated which is preferably used with an optical processing system along the lines of that disclosed in FIG. 15 so as to provide it with an output signal from the detector 30 on the line 110 having the signal values characterized in FIG. 15 for $V_B$, $V_R$, and $V_{X1}, \ldots , V_{XN}$. The video signal on the line 110 is received by an inverting automatic gain control circuit 272 which has its gain adjustable by a signal on a line 274 so as to provide a signal $-V^o(t)$ on the line 276 which is inverted relative to the signal on the line 110 and is adjusted in amplitude according to the signal on line 274. The signal $-V^o(t)$ on the line 276 is received by a sample-and-hold circuit 278 which is gated by the reference sync pulse on line 280 so as to store the reference signal $-V^o_R$. The signal $-V^o(t)$ is also received by a sample-and-hold circuit 282 which is gated by a background sync signal on line 284 so as to store the background signal $-V^o_B$. The background signal $-V^o_B$ is inverted by an inverter 288 to provide a signal $V^o_B$. The reference signal $-V^o_R$ and the background signal $V^o_B$ are received by the inverting terminal of an operational amplifier 286 through respective resistors R. The inverting terminal of the operational amplifier 286 also receives a signal representative of the value "one" from a one-volt internal reference source 290 through a resistor R. The non-inverting terminal of the operational amplifier 286 is connected to ground so that the output of the operational amplifier on the line 274 represents the quantity ($V^o_R$ - $V^o_B$ - 1). The signal representing ($V^o_R$ - $V^o_B$ - 1) on the line 274 is received by the inverting automatic gain control circuit 272 and is effective to adjust the gain of the automatic gain control circuit 272 so that the quantity ($V^o_R$ - $V^o_B$ - 1) is maintained at very nearly zero signal level. The gain of the automatic gain control circuit 272 remains substantially constant between adjustments of the value of the signal ($V^o_R$ - $V^o_B$ - 1) to zero so that the values representative of the components $V_{X1}, \ldots, V_{XN}$ are similarly adjusted in value, i.e., "normalized", by the inverting automatic gain control circuit 272. The superscript "o" for each signal is indicative of the fact that the signals are normalized by transfer through the inverting automatic gain control 272.

A sample gas signal processing circuit 292 is provided for each sample gas $V_{X1}, \ldots, V_{XN}$ to be analyzed. Each sample gas processing circuit 292 receives a signal representative of $-V^o_R$ on line 294 from the sample-and-hold circuit 278, a signal representative of $-V^o_B$ on line 296 from the inverter 288, and a signal representative of $-V^o(t)$ on line 276 from the inverting automatic gain control 272. The signal on line 276 is received by an amplifier circuit 298 which, in effect, multiplies the signal $-V^o(t)$ by a gain K to yield a signal $-KV^o(t)$ on line 300. The signal $-KV^o(t)$ on line 300 is received by a sample-and-hold circuit 302 which is gated by a background sync signal on line 304 so as to provide a signal at its output representative of $-KV^o_B$. The signal $-KV^o(t)$ on line 300 is also received by a sample-and-hold circuit 306 which is gated by a component sync signal on line 308 for gas $X_N$ to provide a signal at its output representative of $-KV^o_X$. The signal representative of $-KV^o_B$ from the sample-and-hold circuit 302 is received by the inverting terminal of an operational amplifier 310 through a resistor R. An output signal representative of $-KV^o_X$ is also received at the inverting terminal of the operational amplifier 310 through an inverter 320 and a resistor R so that the operational amplifier receives a signal representative of $KV^o_X$. The operational amplifier 310 also receives the signal representative of $V^o_B$ on line 298 and a signal representative of $-V^o_R$ through respective resistors R at its inverting terminal whereby each of the signals $KV^o_{X_n}$, $-KV^o_B$, $V^o_B$, and $-V^o_R$ are added at the inverting terminal of the operational amplifier 310. The non-inverting terminal of the operational amplifier 310 is connected to ground so that the output signal of the operational amplifier 310 equals $V^o_R - V^o_B - KV^o_{X_n} + KV^o_B$. The following equals:

$$(V^o_R - V^o_B) - K(V^o_{X_n} - V^o_B) = \frac{(V^o_R - V^o_B) - K(V^o_{X_n} - V^o_B)}{1}$$

$$= \frac{(V^o_R - V^o_B) - K(V^o_{X_n} - V^o_B)}{V^o_R - V^o_B}$$

The last equality holds, since the AGC determines that $V^o_R - V^o_B = 1$.

It should be noted that the systems of this invention provide a measurement of one or all of the component, reference and background energy levels at the detector on each revolution of the filter wheel 75 independently of all previous measurements of those signals. As will be appreciated by the detailed description following, the independent measurement of one or more of those energy levels on each revolution of the filter wheel 75 minimizes systematic errors. In this regard, "systematic" errors are errors which are not random in nature. More particularly, systematic errors are characerized by having a nonzero mean value and can result from nonlinear processing of the detector signal and noise.

Figure 20:
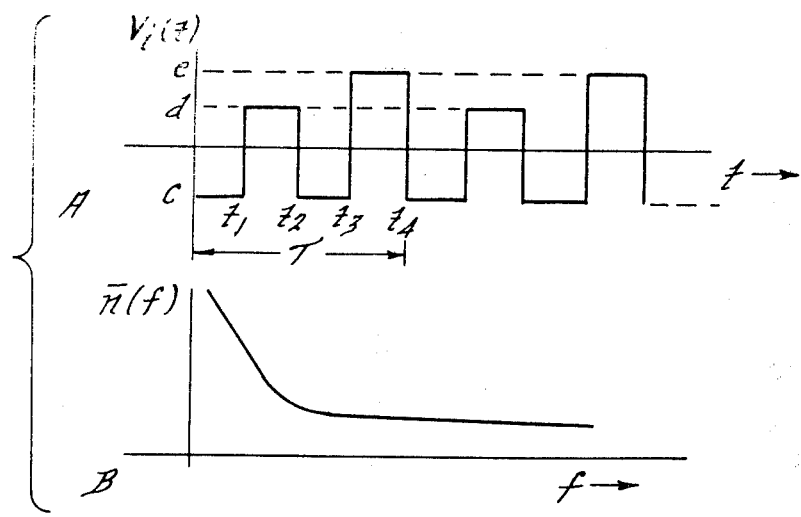
FIG. 20A is an illustration of detector output signal as a function of time and FIG. 20B is an illustration of the detector output signal noise as a function of frequency.

With reference now to FIG. 20a in which the output signal of the detector 30 is represented as a function of time without any noise contribution and FIG. 20b in which the RMS noise contribution of the signal is represented as a function of frequency. Since the noise signal of FIG. 20b is superimposed on the signal of FIG. 20a, the combined signal can be represented as $e(t,f) = V_i(t) + \bar{n}(f)$ where $V_i(t)$ equals a noiseless information-bearing signal and $\bar{n}(f)$ is a noise term superimposed upon $e(t,f), \bar{n}(f)$ has the algebraic form $$\bar{n}(f) = \frac{P_1}{f} + P_2 ,$$

were $P_1$, $P_2$ are constants, $f=$ frequency and $\bar{n}(f)$ has the units of rms volts / $\sqrt{H_z}$ and includes all noise contributions referenced to the amplifier input from the detector, the amplifier, etc. All detectors and amplifying devices can be expected to have noise spectra containing both the $1/f$ and the wideband noise resulting from the $P_2$ term.

$V_i(t)$ is considered to be made up of square pulses. Let the signal between $t_1$ and $t_2$ be the reference signal and let the signal between $t_3$ and $t_4$ be the sample signal.

Figure 21:
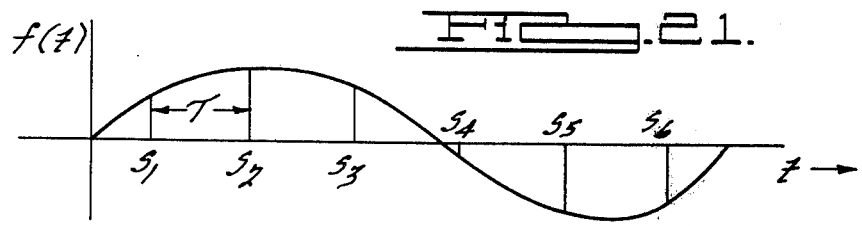
FIG. 21 is an illustration of a low frequency component of noise of the detector output signal.
Figure 22:
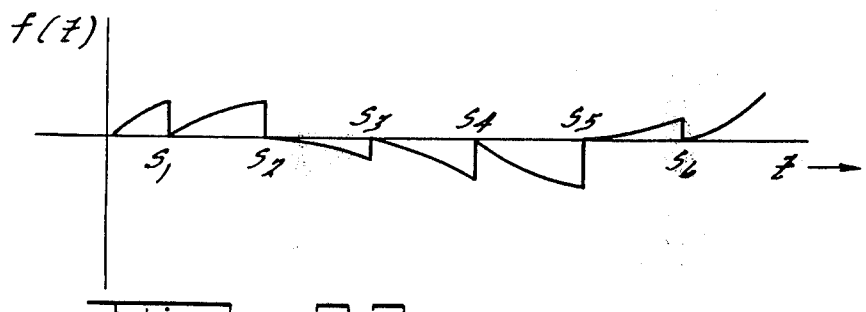
FIG. 22 is a graphic illustration of the low frequency component of noise of FIG. 21 after background compensation by the signal processing circuitry of either FIG. 15 or FIG. 19.

As described herein, a voltage level representative of background level is sampled once during every signal period $\tau$. This is essentially a discrete sampling, accomplished via a sample-and-hold circuit whose aperture time is much, much less than $\tau$. The sample value is immediately subtracted from the rest of the video signal, or, equivalently, all of its relevant component parts, and this subtracted voltage level is impressed upon the video signal until a new background level is obtained, the process then repeating. In addition to compensating for background level, however, this method has the very important property of rejecting low-frequency noise. Consider a noise waveform as shown in FIG. 21, with the sampling times spaced $\tau$ apart. The action of the background compensation circuit is such that the voltage of the waveform is adjusted to zero at $t = s_1, s_2, \ldots$. Thus the waveform above is transformed into the waveform shown in FIG. 22. The rms value of this last waveform is equal to or less than the rms value of the waveform from which it was derived, depending upon the relationship of $\tau$ and $f$.

Figure 23:
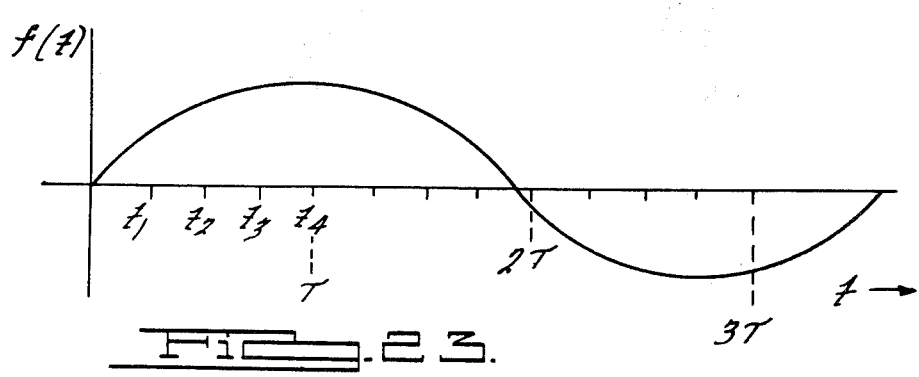
FIG. 23 is yet another illustration of a low frequency component of noise of the detector output signal.

In particular, consider a sinusoidal waveform a sin wt represented on the same time scale as is $V_i(t)$ in FIG. 20a, and shown with appropriate time indications in FIG. 23. The background level is sampled within the invervals $\{o, t\}, \{\tau, \tau + t\}, \{2\tau, 2\tau + t\}, \ldots$. Arbitrarily let $t = \frac{1}{2}t$, so that these sample times are $\frac{1}{2}t_1, \tau + \frac{1}{2}t_1, 2\tau + \frac{1}{2}t_1, \ldots$. The rms noise level which exists at some subsequent sampling times $\frac{1}{2}t_1 + K\tau, \tau + \frac{1}{2}t_1 + K\tau, \ldots$, $(K < 1)$, can be obtained as follows. The level of the noise $\epsilon$ within each period at the times defined above can be obtained as:

$\epsilon_1 = a \sin w [\frac{1}{2}t_1 + K\tau] - a \sin w [\frac{1}{2}t_1]$ $\epsilon_2 = a \sin w [\frac{1}{2}t_1 + \tau + K\tau] - a \sin w [\frac{1}{2}t_1 + \tau]$ $\epsilon_3 = a \sin w [\frac{1}{2}t_1 + 2\tau + K\tau] - a \sin w [\frac{1}{2}t_1 + 2\tau]$ $\epsilon_n = a \sin w [\frac{1}{2}t_1 + (n-1)\tau + K\tau] - a \sin w [\frac{1}{2}t_1 + (n-1)\tau]$ The rms of the noise at any periodic sampling time $\frac{1}{2}t_1 + M\tau$, where M is any integer, can be defined as:

$$\bar{\epsilon}(w, K, \tau) = \lim_{N \to \infty} \sqrt{\frac{\sum_{n=1}^{N} \epsilon_n^2}{N}}$$

$$= a \lim_{N \to \infty} \sqrt{\frac{\sum_{n=1}^{N} \{\sin w [\frac{1}{2}t_1 + (n-1)\tau + K\tau] - \sin w [\frac{1}{2}t_1 + (n-1)\tau]\}}{N}}$$

via the relation $\sin A - \sin B = 2 \sin \frac{1}{2}(A-B) \cos \frac{1}{2}(A+B)$ $$\bar{\epsilon} = 2a \left| \sin \frac{1}{2} wK\tau \right| \lim_{N \to \infty} \sqrt{\frac{\sum_{n=1}^{N} \cos^2 \frac{1}{2} w[t_1 + 2(n-1)\tau + K\tau]}{N}}$$

via the relation $\cos^2 A = \frac{1}{2} + \frac{1}{2} \cos 2A$ $$\bar{\epsilon} = \sqrt{2} a \left| \sin \frac{1}{2} Kw\tau \right| \lim_{N \to \infty} \sqrt{\frac{N + \sum_{n=1}^{N} \cos w [t_1 + 2(n-1) + K\tau]}{N}}$$

If $$\frac{w}{t_1 + 2(n-1) + K\tau}$$

is irrational, then the summation over N as $N \to \infty$ is finite, and $$\bar{\epsilon} = \sqrt{2} a \left| \sin \frac{1}{2} Kw\tau \right|.$$

If it is rational, however, it would appear that the summation becomes infinite as $N \to \infty$. If one keeps in mind the fact that noise of a given frequency is of random phase, the summation of the cosine terms with a random phase term inserted into its argument remains finite as $N \to \infty$, and thus one obtains the same result $$\epsilon(w, K, \tau) = \sqrt{2} a \left| \sin \frac{1}{2} Kw\tau \right|$$

or, with $$\tau = \frac{2\pi}{w_c},$$

where $w_c$ = sampling rate, $$\epsilon(w, w_c, K) = \sqrt{2} a \left| \sin K\pi \frac{w}{w_c} \right|$$

Thus, noise is rejected according to the relation above. More particularly, low frequency noise, i.e. that noise which extends from DC to approximately $2\pi$ times the sampling frequency, is removed by the signal manipulating steps in the processing circuits. This is accomplished by measuring each of the component, reference and background signals independently of all previous measurements of the component reference and background signals on each cycle and subtracting the background signal from at least one other signal on each cycle so that the DC component of noise and a substantial portion of the low frequency component of noise is removed by the subtraction on each cycle. In the present system, there are no systematic errors since the mean noise level is zero. Consequently, if the output signal is time averaged over a sufficiently long time, an error-free signal can be obtained. With regard to the rejection of high frequency noise, that is, noise appearing at frequencies greater than $2\pi$ times the sampling rate, appropriate noise rejection can be obtained using a low-pass filter after demodulation of the video train from the detector 30. More specifically, after the video signal has been background compensated (with low-frequency noise being rejected as above) and the video signal has been normalized to the reference level, the sample signal is demodulated, again via discrete sampling. The demodulated sample signal is subtracted from the reference level and the resulting signal passes through an $n^{th}$ order low-pass filter to the output. With respect to noise considerations, if the break point of this low-pass filter is $w_H$ then this is equivalent to applying a filter of order n with break point at $(w_c + w_H)$ to the video signal.

In view of the above, it will be appreciated that the overall noise rejection of the system is as follows:

$$\frac{\text{noise out } (w)}{\text{noise in } (w)} = \sqrt{2} \left| \sin K\pi \frac{w}{w_c} \right| \frac{1}{[1 + \frac{w^2}{(w_c + w_H)^2}]^{\frac{n}{2}}}$$

While it will be apparent that the teachings herein are well calculated to teach the method of making the preferred embodiment of this invention to one skilled in the art, it will be appreciated that the invention is susceptible to modification, variation and change without departing from the proper scope or meaning of the subjoined claims.

We claim:

1. A spectrophotometer having chamber means for containing a fluid for analysis, indicating means for indicating the concentration of a component of said fluid, and an adjustable calibration control for setting said indicating means to a zero indication while a substantially nonabsorbing fluid is contained in said chamber comprising:
   means providing a component signal which is related to the concentration of said component of said fluid;
   means providing a reference signal;
   means for providing a component ratio signal representative of the ratio of said component signal with respect to said reference signal including adjustment means receiving said component signal and said reference signal for adjusting said reference signal so that said reference signal represents a predetermined standard value, said adjustment means adjusting said component signal an amount correlative to said adjustment of said reference signal to provide said component ratio signal;
   means for reducing said component ratio signal an amount representative of said standard value to provide a reduced component ratio signal; and
   means associated with said adjustable calibration control and said indicating means for adjusting said reduced component ratio signal and providing for the indication thereof by said indicating means in a manner so that said indication indicates zero when said substantially non-absorbing fluid is in said chamber, said adjustable calibration control and said means associated with said adjustable calibration control being adapted to be invariant when said fluid having said component is analyzed so that said indicating means indicates the concentration of said component in said fluid.

2. A spectrophotometer of claim 1 wherein said means associated with said adjustable calibration control includes a variable resistor which receives and reduces said reduced component ratio signal.

3. A spectrophotometer according to claim 1 wherein said standard value represents a value of unity.

4. A spectrophotometer according to claim 1 wherein said means for providing a reduced component ratio signal subtracts said standard value from said component ratio signal.

5. A spectrophotometer having chamber means for containing a fluid for analysis and readout means for indicating concentration result of said analysis, said readout means including known concentration scale span graduations, said graduations being invariant, an adjustable calibration control for adjusting the indications of said readout means to indicate a zero concentration while a substantially nonabsorbing fluid is in said chamber, said spectrophotometer comprising:
   means providing a component signal which is related to the concentration of said component of said fluid;
   means providing a reference signal;
   means for providing a component signal representative of the ratio of said component signal with respect to said reference signal including adjustment means receiving said component signal for adjusting said component signal an amount correlative to the difference between said reference signal and a predetermined standard value to provide said component ratio signal;
   means for reducing said component ratio signal an amount representative of said standard value to provide a reduced component ratio signal including means associated with said adjustable calibration control for adjusting said reduced component ratio signal and for providing for the indication thereof by said readout means in a manner so that said indication indicates zero when said substantially non-absorbing fluid is in said chamber, said adjustable calibration control and said means associated with said adjustable calibration control being adapted to be invariant when said fluid having said component is analyzed so that said readout means indicates the concentration of said component in said fluid.

6. A spectrophotometer according to claim 5 wherein said standard value represents a value of unity.

7. A spectrophotometer according to claim 5 wherein said means for providing a reduced component ratio signal subtracts said standard value from said component ratio signal.

8. A spectrophotometer of claim 5 wherein said means associated with said adjustable calibration control includes a variable resistor which receives and reduces said reduced component ratio signal.

9. A spectrophotometer of claim 8 wherein said substantially nonabsorbing fluid is air.

10. A method for analyzing fluid to determine the concentration of a component therein utilizing a spectrophotometer which includes a chamber and an output signal indicator which is adapted to provide a zero concentration indication and a plurality of indications representing preselected concentrations of said component comprising the steps of:

introducing a substantially non-absorbing gas into said chamber;

obtaining the transmissivity of energy through said substantially non-absorbing gas exclusive of background radiation at a first band of wave lengths at which said component has substantial influence and referencing said transmissivity to the transmissivity of said energy through said substantially non-absorbing gas at a second band of wave lengths at which said component has substantially less influence;

adjusting said spectrophotometer with said substantially non-absorbing fluid in said chamber so that said output signal indicator provides a zero concentration indication;

introducing a fluid to be analyzed into said chamber;

obtaining the transmissivity of energy through said fluid to be analyzed exclusive of background radiation at said first band of wave lengths at which said component has substantial influence and referencing said transmissivity reading to the transmissivity of said energy through said fluid to be analyzed at said second band of wave lengths at which said component has substantially less influence; and reading the indication of said output signal indicator with said fluid to be analyzed in said chamber.

11. The method of claim 10 wherein said first and second bands of wave lengths are in the infrared energy band.

12. The method according to claim 10 wherein said transmissivity at said first band of wave lengths is referenced to said transmissivity at said second band of wave lengths by obtaining the ratio of said transmissivity at said first band of wave lengths with respect to said transmissivity at said second band of wave lengths.

13. A method according to claim 10 wherein said substantially non-absorbing gas is atmospheric air.

14. A method for calibrating an analyzer and determining the concentration of a component of a gas using the analyzer comprising the steps of:

introducing atmospheric air into a sample volume;

determining the transmissivity of energy through said atmospheric air at a predetermined component band of wave lengths at which said component has a substantial absorption of said energy;

determining the transmissivity of said energy through said atmospheric air at a predetermined reference band of wave lengths at which said component has substantially less absorption of said energy;

determining the background radiation;

subtracting said determination of background radiation from said determination of component transmissivity for atmospheric air to yield an atmospheric air background compensated component transmissivity determination and subtracting said determination of background transmissivity for atmospheric air from said reference transmissivity determination for atmospheric air to yield an atmospheric air background compensated reference transmissivity determination;

determining the ratio of said atmospheric air background compensated component transmissivity determination and said atmospheric air background compensated reference transmissivity determination to yield an atmospheric air ratio determination;

transmitting said atmospheric air ratio determination to an indicator thereof;

adusting the indication of said atmospheric air ratio so that the indication thereof represents a zero indication;

introducing said gas into said sample volume;

determining the transmissivity of energy through said gas at a predetermined component band of wave lengths at which said component has a substantial absorption of said energy;

determining the transmissivity of said energy through said gas at a predetermined reference band of wave lengths at which said component has substantially less absorption of said energy;

subtracting said determination of background radiation from said determination of component transmissivity for said gas to yield a gas background compensated component transmissivity determination and subtracting said determination of background transmissivity for said gas from said reference transmissivity determination for said gas to yield a gas background compensated reference transmissivity determination;

determining the ratio of said gas background compensated component transmissivity determination and said gas background compensated reference transmissivity determination to yield a gas ratio determination; and transmitting said gas ratio determination to said indicator thereof without altering the adjustment made for the indication of said atmospheric air ratio determination so that a non-zero indication represents the concentration of said component of said gas.

15. The method of claim 14 wherein said background radiation for said atmospheric air and for said gas is obtained by blocking said energy.

16. The method of claim 14 wherein the determinations of the transmissivity of energy through said atmospheric air and through said gas at said component and reference bands of wave lengths are made in the infrared energy band.

17. The method of claim 14 wherein the determinations of the transmissivity of energy through said atmospheric air and through said gas at said component and reference bands of wave lengths are made solely in the infrared energy band.

18. The method of claim 14 further including the step of determining the transmissivity of energy through said gas at a predetermined second component band of wave lengths at which a second component of said gas has a substantial absorption of energy.

19. The method of claim 18 further including the steps of compensating said gas ratio determination for said first mentioned component in accordance with the transmissivity of said energy through said gas at said predetermined second component band of wave lengths.

20. A method for calibrating an analyzer and determining the concentration of first and second components of a gas using the analyzer comprising the steps of:

introducing atmospheric air into a simple volume;

determining the transmissivity of energy through said atmospheric air at a predetermined first component band of wave lengths at which said first component has a substantial absorption of said energy;

determining the transmissivity of energy through said atmospheric air at a predetermined second component band of wave lengths at which said second component has a substantial absorption of said energy;

determining the transmissivity of said energy through said atmospheric air at predetermined reference wave lengths at which said first and second components have substantially less absorption of said energy;

determining the background radiation;

subtracting said determination of background radiation from said determination of first component transmissivity for atmospheric air to yield an atmospheric air background compensated first component transmissivity determination, subtracting said determination of background radiation from said determination of second component transmissivity for atmospheric air to yield an atmospheric air background compensated second component transmissivity determination, and subtracting said determination of background transmissivity for atmospheric air from said reference transmissivity determination for atmospheric air to yield an atmospheric air background compensated reference transmissivity determination;

determining the ratio of said atmospheric air background compensated first component transmissivity determination and said atmospheric air background compensated reference transmissivity determination to yield an atmospheric air first component ratio determination;

determining the ratio of said atmospheric air background compensated second component transmissivity determination and said atmospheric air background compensated reference transmissivity determination to yield an atmospheric air second component ratio determination;

transmitting said atmospheric air first component ratio determination to a first component indicator;

adjusting the indication of said atmospheric air first component ratio so that the indication thereof represents a zero indication;

transmitting said atmospheric air second component ratio determination to a second component indicator;

adjusting the indication of said atmospheric air second component ratio so that the indication thereof represents a zero indication;

introducing said gas into said sample volume;

determining the transmissivity of energy through said gas at a predetermined first component band of wave lengths at which said first component has a substantial absorption of said energy;

determining the transmissivity of energy through said gas at a predetermined second component band of wave lengths at which said second component has a substantial absorption of said energy;

determining the transmissivity of said energy through said gas at predetermined reference wave lengths at which said first and second components have substantially less absorption of said energy;

subtracting said determination of background radiation from said determination of first component transmissivity for said gas to yield a gas background compensated first component transmissivity determination, subtracting said determination of background radiation from said determination of second component transmissivity for said gas to yield a gas background compensated second component transmissivity determination, and subtracting said determination of background transmissivity for said gas from said reference transmissivity determination for said gas to yield a gas background compensated reference transmissivity determination;

determining the ratio of said gas background compensated first component transmissivity determination and said gas background compensated reference transmissivity determination to yield a gas first component ratio determination;

determining the ratio of said gas background compensated second component transmissivity determination and said gas background compensated reference transmissivity determination to yield a gas second component ratio determination;

transmitting said gas first component ratio determination to said first component indicator without altering the adjustment made for the indication of said atmospheric air first component ratio determination so that a non-zero indication represents the concentration of said first component of said gas; and transmitting said gas second component ratio determination to said second component indicator without altering the adjustment made for the indication of said atmospheric air second component ratio determination so that a non-zero indication represents the concentration of said second component of said gas.

21. The method according to claim 20 including the step of compensating said gas first component ratio determination in accordance with said gas second component ratio determination.

22. The method of claim 20 wherein said background radiation for said atmospheric air and for said gas is obtained by blocking said energy.

23. The method of claim 20 wherein the determinations of the transmissivity of energy through said atmospheric air and through said gas at said first component, second component, and reference bands of wave lengths are made in the infrared energy band.

24. The method of claim 20 wherein the determinations of the transmissivity of energy through said atmospheric air and through said gas at said first component, second component, and reference bands of wave lengths are made solely in the infrared energy band.

25. A method for calibrating an analyzer and determining the concentration of a component of a gas using the analyzer comprising the steps of:

introducing atmospheric air into a sample volume;

determining the transmissivity of energy through said atmospheric air at a predetermined component band of wave lengths at which said component has a substantial absorption of said energy;

determining the transmissivity of said energy through said atmospheric air at a predetermined reference band of wave lengths at which said component has substantially less absorption of said energy;

compensating said atmospheric air determination of component transmissivity for background radiation to yield an atmospheric air background compensated component transmissivity determination and compensating said atmospheric air reference transmissivity determination for background radiation to yield an atmospheric air background compensated reference transmissivity determination;

determining the ratio of said atmospheric air background compensated component transmssivity determination and said atmospheric air background compensated reference transmissivity determination to yield an atmospheric air ratio determination;

indicating said atmospheric air ratio determination and adjusting the indication of said atmospheric air ratio so that the indication thereof represents a zero indication;

introducing said gas into said sample volume;

determining the transmissivity of energy through said gas at a predetermined component band of wave lengths at which said component has a substantial absorption of said energy;

determining the transmissivity of said energy through said gas at a predetermined reference band of wave lengths at which said component has substantially less absorption of said energy;

compensating said gas determination of component transmissivity for background radiation to yield a gas background compensated component transmissivity determination and compensating said gas reference transmissivity determination for background radiation to yield a gas background compensated reference transmissivity determination;

determining the ratio of said gas background compensated component transmissivity determination and said gas background compensated reference transmissivity determination to yield a gas ratio determination; and indicating said gas ratio determination using the same adjustment made for the indication of said atmospheric air ratio so that a non-zero indication represents the concentration of said component of said gas.

26. The method of claim 25 wherein said background radiation for said atmospheric air and for said gas is obtained by blocking said energy.

27. The method of claim 25 wherein the determinations of the transmissivity of energy through said atmospheric air and through said gas at said component and reference bands of wave lengths are made in the infrared energy band.

28. The method of claim 25 wherein the determinations of the transmissivity of energy through said atmospheric air and through said gas at said component and reference bands of wave lengths are made solely in the infrared energy band.

* * * * *

UNITED STATES PATENT AND TRADEMARK OFFICE
CERTIFICATE OF CORRECTION

PATENT NO. : 3,979,589

DATED : September 7, 1976

INVENTOR(S) : Stanley R. Sternberg et al

It is certified that error appears in the above-identified patent and that said Letters Patent are hereby corrected as shown below:

Column 2, line 24, "means" should be --mean--.
Column 4, lines 6-7, delete "cell transmitted" (2nd occurrence).
Column 7, line 19, "-9 d" should be --] $d\lambda$ --.
Column 8, line 3, after "]-" insert --$\int$--.
Column 8, line 8 (3rd line of equation), "$T_o(\lambda)$" should be --$T_o(\lambda)$--.
Column 10, line 31, "numberals" should be --numerals--.
Column 12, line 51, "the" should be --an--.
Column 14, line 58, "compound" should be --component--.

Column 20, line 66, "$sk\overline{W}$" should be --$s\overline{KW}$--.

Column 21, line 1, "W" should be --$\overline{W}$--.
Column 21, line 9, "j=1 ...,N" should be --j=1,...,N--.
Column 21, line 20, "$-K_X$" should be -- $-K_{X_1}$ --.

Column 21, line 23, "smaple" should be --sample--.
Column 21, line 27, "$K_X$" should be --$K_{X_i}$--.

Column 23, line 56, "$-V^o_B$" should be --$V^o_B$--.

Column 24, lines 1 and 5, "$-KV^o_X$" should be -- $-KV^o_{X_N}$ --.

Column 24, line 8, "$KV^o_X$" should be --$KV^o_{X_N}$--.

Column 24, line 17, "$KV^o_{Xn}$" should be --$KV^o_{X_N}$--.

Column 24, line 21, (1st occurrence) "$KV^o_{Xn}$" should be --$KV^o_{X_N}$--.

UNITED STATES PATENT AND TRADEMARK OFFICE
CERTIFICATE OF CORRECTION

PATENT NO. : 3,979,589
DATED : September 7, 1976
INVENTOR(S) : Stanley R. Sternberg et al It is certified that error appears in the above-identified patent and that said Letters Patent are hereby corrected as shown below:

Column 24, line 21 "$\dfrac{(V^o_R - V^o_B) - K(V^o - V^o_B)}{1 \quad X_n}$" should be --$\dfrac{(V^o_R - V^o_B) - K(V^o_{X_N} - V^o_B)}{1}$--.

Column 24, line 23 "$\dfrac{(V^o_R - V^o_B) - K(V^o - V^o_B)}{V^o_R - V^o_B \qquad X_n}$" should be --$\dfrac{(V^o_R - V^o_B - K(V^o_{X_N} - V^o_B)}{V^o_R - V^o_B}$--.

Column 25, line 43, after "rms" insert --value--.

Column 30, line 66, Claim 20, line 5, "simple" should be --sample--.

Signed and Sealed this

Twenty-eighth Day of June 1977

[SEAL]

Attest:

RUTH C. MASON
Attesting Officer

C. MARSHALL DANN
Commissioner of Patents and Trademarks